US007684867B2

(12) United States Patent
Jaax et al.

(10) Patent No.: US 7,684,867 B2
(45) Date of Patent: Mar. 23, 2010

(54) TREATMENT OF APHASIA BY ELECTRICAL STIMULATION AND/OR DRUG INFUSION

(75) Inventors: Kristen N. Jaax, Saugus, CA (US); Rafael Carbunaru, Santa Clarita, CA (US); Todd K. Whitehurst, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 766 days.

(21) Appl. No.: 11/264,436

(22) Filed: Nov. 1, 2005

(65) Prior Publication Data

US 2007/0100389 A1    May 3, 2007

(51) Int. Cl.
*A61N 1/00* (2006.01)
(52) U.S. Cl. ............................... 607/45; 607/3
(58) Field of Classification Search ............ 600/378; 607/45, 2, 3
See application file for complete search history.

(56) References Cited

U.S. PATENT DOCUMENTS

| 4,431,000 | A | | 2/1984 | Butler et al. ............... 128/421 |
|---|---|---|---|---|
| 6,132,361 | A | | 10/2000 | Epstein et al. ............... 600/13 |
| 6,164,284 | A | * | 12/2000 | Schulman et al. ........... 128/899 |
| 6,920,359 | B2 | | 7/2005 | Meadows et al. ............. 607/59 |
| 6,944,497 | B2 | * | 9/2005 | Stypulkowski ............... 607/2 |
| 2002/0013612 | A1 | * | 1/2002 | Whitehurst ............... 607/45 |
| 2005/0027284 | A1 | * | 2/2005 | Lozano et al. ........... 604/890.1 |
| 2006/0212090 | A1 | * | 9/2006 | Lozano et al. ............... 607/45 |

FOREIGN PATENT DOCUMENTS

WO     WO 2004052449 A1 *  6/2004

OTHER PUBLICATIONS

Albert "Treatment of Aphasia [Neurological Review]" Archives of Neurology 55(11) (1998) 1417-1419.
Kreisler, et al. "The Anatomy Of Aphasia Revisited" Neurology 54(5) (2000) 1117-1123.
Lucas, et al. "Functional Separation Of Languages In The Bilingual Brain: A Comparison Of Electrical Stimulation Language Mapping In 25 Bilingual Patients And 117 Monolingual Control Patients" J. Neurosurg. 101 (2004) 446-457.
Martin, et al. "Transcranial Magnetic Stimulation As a Complementary Treatment for Aphasia" Seminars in Speech and Language 25 (2) (2004) 181-191.

(Continued)

*Primary Examiner*—Scott M Getzow
(74) *Attorney, Agent, or Firm*—Vista IP Law Group LLP

(57) ABSTRACT

Systems and methods are provided for applying electrical stimulation and/or introducing one or more stimulating drugs to the brain to treat or prevent aphasia, including through use of at least one system control unit (SCU) for controlling electrical pulses delivered via electrodes implanted in the brain and/or for producing drug infusion pulses to targeted areas in the brain.

14 Claims, 11 Drawing Sheets

OTHER PUBLICATIONS

Mottaghy, et al. "Facilitation of Picture Naming After Repetitive Transcranial magnetic Stimulation" Neurology 53(8) (1999) 1806-1812.

Nikas, et al. "Tumor Surgery Under Local Anesthesia;" Techniques in Neurosurgery 7 (2001) 70-84.

Randolph, et al. "Role of Adaptive Plasticity in Recovery of Function After Damage to Motor Cortex" Muscle & Nerve 24 (2001) 1000-1019.

Ojemann, et al. "Cortical Language Localization in Left, Dominant Hemishpere;" J. Neurosurg. 71 (1989) 316-1989.

Pouratian, et al. "Variability of Intraoperative Electrocortical Stimulation Mapping Parameters Across and Within Individuals" J. Neurosurg. 101 (2004) 458-466.

Quigg, et al. "Conduction Aphasia Elicited by Stimulation of the Left Posterior Superior Temporal Gyrus" J Neurol Neurosurg Psychiatry 66 (1999) 393-396.

Robles, et al.; "The Role Of Dominant Stratum In Language: A Study Using Intraoperative Electrical Stimulations" J. Neurol Neurosurg Psychiatry 76 (2005) 940-946.

Schäffler, et al. "Quantitiative Comparison of Language Deficits Produced by Extraoperative electrical Stimulation of Broca's, Wernicke's, and Basal Temporal Language Areas" Epilepsia 37(5) (1996) 463-475.

Zahn, et al. "Recovery of Semantic Word Processing in Global Aphasia: A Functional MRI Study" Cognitive Brain Research 18 (2004) 322-336.

* cited by examiner

TREATMENT OF APHASIA BY ELECTRICAL STIMULATION AND/OR DRUG INFUSION

FIELD OF THE INVENTION

The present invention generally relates to drug delivery and electrical stimulation systems and methods, and more particularly relates to utilizing one or more devices to deliver electrical stimulation and/or one or more stimulating drugs to certain areas of the brain as a treatment for aphasia.

BACKGROUND OF THE INVENTION

Aphasia is impairment in a patient's ability to use language and may affect comprehension of speech, production of speech and the capacity to read or write. It occurs as a result of injury to the brain, commonly due to stroke, but also secondary to trauma, brain tumors, infection and dementia. Current estimates provide that 700,000 people suffer a stroke each year in the U.S. and that approximately two-thirds of these individuals survive and require rehabilitation. At least one-fourth of all stroke survivors experience language impairments involving the ability to speak, write, and understand spoken and written language. Aphasia, typically as a consequence of stroke, is estimated to affect 1 million Americans. (Albert, M L. *Archives of Neurology* 55(11)(1998) 1417-9.).

Aphasia has been categorized into several distinct diseases, including Broca's, Wernicke's, conductive, anomic and transcortical aphasia. In Broca's aphasia, also termed expressive, motor or anterior aphasia, comprehension is largely intact but oral and written communication is impaired. The patient thus communicates by nonfluent or impaired expression of either spoken or written language. Global aphasia is characterized by loss of all ability to communicate and typically results from extensive anterior-posterior lesions of the dominant (typically left) hemisphere.

Wemicke aphasia, also called receptive, sensory or posterior aphasia, is caused most often by occlusion of the lower division of the middle cerebral artery (MCA) bifurcation or one of its branches. These patients vocalize smoothly and with expression, but their speech is characterized by distorted phonetic structure, word substitution, and additional prefixes and suffixes. Although fluent in speech, the words produced are not understandable. Wernicke's area of the brain is located in the temporal lobe of the cortex near brain regions involved in processing sound inputs. The infarct responsible for a classic Wernicke's aphasia includes the dominant (typically left-sided) posterior temporal, inferior parietal and lateral temporal-occipital regions.

Conductive aphasia, also called associative aphasia, has been classically thought to be caused-by a disruption of the dominant (typically left) arcuate fasciculus or supramarginal gyrus extending to the temporal cortex. Patients with conductive aphasia have significant difficulty repeating unfamiliar phrases and words but demonstrate much better auditory and written comprehension compared to individuals with Wernicke's aphasia and are more likely to recognize the deficit and make an effort to self-correct. Damage to the language areas of the left hemisphere that are outside the primary language areas results in transcortical aphasia.

Anomic aphasia, also called nominal aphasia, also primarily influences the ability to fmd the right name for a person or object. Anomia is caused by damage to various parts of the parietal or temporal lobe and usually involves a breakdown in one or more pathways or connectivity patterns (diaschisis) between regions in the brain. Averbia is a specific type of anomia characterized by trouble remembering only verbs. Averbia is caused by damage to the frontal cortex in or near Broca's area.

In transcortical motor aphasia, transcortical sensory aphasia, and mixed transcortical aphasia, the patient has either partial or total loss of the ability to communicate verbally or using written words but is able to repeat words, phrases, or sentences.

Current accepted treatments for rehabilitation of aphasia include cognitive neurorehabilitation, computer-aided techniques, psycholinguistic theory-driven therapy, psychosocial management and pharmacotherapy. No pharmacotherapies are able to cure aphasia. Surgery is not useful in aphasia secondary to stroke, though aphasia due to a tumor or hematoma compressing a critical speech center may be responsive to surgery. Speech therapy is offered to aphasic patients for the purpose of developing full utilization of their remaining skills and to develop compensatory mechanisms for communicating.

Experimental therapies that have been proposed or tried in treatment of aphasia include transcranial magnetic stimulation (TMS). See, e.g., Epstein and Davey, U.S. Pat. No. 6,132, 361. Experimental application of this technique for stimulation of region of the cortex shown to be hyperactive during aphasia has indicated significant improvement in naming pictures following 10 TMS treatments in a total of 4 patients. Martin P I, et al. *Semin Speech Lang.* 2004 25(2): 181-91. Similarly, TMS has been used to stimulate Wernicke's area, the right-hemisphere homologue of Wernicke's area, Broca's area, and the primary visual cortex in treatment of aphasia. Picture naming was reported to be facilitated after repetitive TMS. Mottaghy F M, et al. *Neurology* 53(8)(1999) 1806-12. Transcutaneous nerve stimulation by generation of trapezoidal mono-phasic pulses to the skin such as the skin of the arm was proposed in Butler et al., U.S. Pat. No. 4,431,000, but does not appear to have been sufficiently successful to have entered the treatment armamentarium for aphasia.

Further treatments for aphasia are clearly needed.

BRIEF SUMMARY OF THE INVENTION

The invention disclosed and claimed herein provides systems and methods for introducing one or more stimulating substances and/or applying electrical stimulation to one or more areas of the brain for treating or preventing aphasia, as well as the symptoms and pathological consequences thereof.

In one embodiment of the invention a method of treating a communication disorder in an aphasia patient is provided that includes implantation of at least one System Control Unit (SCU) controllably connected to one or more electrodes and/ or infusion outlets. Although the SCU may be remote from the area to be stimulated, the electrodes and/or infusion outlets are implanted in or adjacent to one or more language areas of the aphasia patient's brain.

Implantation areas for the electrodes and/or infusion outlets include the insula, frontoparietal operculum, posterior temporal cortex, inferior parietal cortex, lateral temporal-occipital cortex, arcuate fasciculus, thalamus, superior temporal gyrus, extrasylvian posterior temporal cortex, posterior parietal cortex, Broca's area, pre-Rolandic gyrus, Wernicke's area, putamen, and combinations thereof Optionally, the SCU is connected to or comprises at least one pump that is operably connected to the infusion outlets and the stimulus includes stimulation via one or more drugs delivered to language areas through action of the pump.

In one embodiment of the invention, the Broca's area stimulus is applied to at least the posterior inferior frontal gyrus region of Broca's area, while the pre-Rolandic gyrus stimulus is applied to at least the inferior precentral region of the pre-Rolandic gyrus. Where the aphasia is Wernicke's aphasia, the stimulus preferably applied to at least one of the posterior-temporal cortex, posterior parietal cortex, inferior parietal cortex, and extrasylvian posterior temporal cortex. In one embodiment, the stimulus is applied to the right posterior parietal cortex.

In another embodiment of the invention, an aphasia treatment system is provided that includes at least one system control unit (SCU) having a replenishable power source; at least one electrode in electrical communication with the SCU and adapted for implantation in one or more language areas of the brain, and an external battery charger. At least one of the SCU may provide a multiplicity of stimulation channels, wherein each stimulation channel is independently programmable with different stimulation parameters including one or more of: pulsewidth, stimulation amplitude, repetition rate or pulses per second (pps), and an electrode configuration that may be either monopolar or bipolar. In other embodiments, the SCU includes processing circuitry including: a control logic circuit, a timer logic circuit, a microcontroller circuit, and a memory circuit coupled to the microcontroller circuit; and wherein the control logic, timer logic and microcontroller circuits are responsive to programming signals stored in the memory circuit to generate stimulation pulses having a specified amplitude, pulsewidth and repetition rate (pps).

In one embodiment, the SCU includes electrical circuitry that receives power and/or receives or transmits data by inductive or radio-frequency (RF) coupling to a transmitting coil placed outside the body.

Some forms of SCUs may include any of the following structures in any enabling combination: implantable signal/pulse generators (IPGs), implantable pumps, IPG/pump combinations, microstimulators for drug and/or electrical stimulation, including miniature implantable neurostimulators, such as a Bionic Neuron (also referred to as a BION® microstimulator), and other alternative devices described herein, and the like. The SCU are operably connected to one or more electrodes that are surgically implanted to provide electrical stimulation, one or more infusion outlets and/or catheters that are surgically implanted to infuse drug(s) from an implantable pump. The systems of the invention may also include one or more sensors for sensing symptoms or conditions that may indicate a needed treatment.

An SCU may-control delivery of electrical stimulation and/or one or-more stimulating drugs when necessary and/or desired. In some embodiments, the SCU is implanted in a surgically-created shallow depression or opening in the skull, such as in the temporal, parietal, or frontal bone. In some such embodiments, one or more electrode leads and/or catheters attached to the SCU run subcutaneously to an opening in the skull and pass through the opening into or onto the cortex and/or Deep Brain parenchyma and surrounding tissue.

Patients with aphasia will likely respond to therapeutic excitatory stimulation applied to those areas of the brain that exhibit chronic decreased activity relative to normal control subjects. Thus, according to certain embodiments of the invention, the stimulation increases excitement of one or more of those areas of the brain that exhibit chronic decreased activity in patients relative to normal control subjects, thereby treating or preventing aphasia and/or the consequences thereof. Such excitatory stimulation is likely to be produced by, for example, low-frequency electrical stimulation, an excitatory neurotransmitter agonist, and/or an excitatory hormone agonist. For example, relatively low frequency neurostimulation (i.e., less than about 100 Hz in the brain) typically has an excitatory effect on surrounding neural tissue, leading to increased neural activity, whereas relatively high frequency neurostimulation (i.e., greater than about 100 Hz in the brain) may have an inhibitory effect, leading to decreased neural activity.

Patients with aphasia will likely respond to therapeutic inhibitory stimulation applied to those areas of the brain that exhibit chronic increased activity relative to normal control subjects. Thus, according to various embodiments of the invention, the stimulation decreases excitement of one or more of those areas of the brain that exhibit chronic increased activity in patients relative to normal control subjects, thereby treating or preventing aphasia and/or the consequences thereof. Such inhibitory stimulation is likely to be produced by, for example, high-frequency electrical stimulation, an inhibitory neurotransmitter agonist, and/or an inhibitory hormone agonist.

The SCU may include a programmable memory for storing data and/or control parameters. This allows stimulation and control parameters to be adjusted to levels that are safe and efficacious with minimal discomfort. Electrical and drug stimulation may be controlled independently. Alternatively, electrical and drug-stimulation may be coupled, e.g., electrical stimulation may be programmed to occur only during drug infusion. Programmable SCU controlling electrical stimulation and or pump mediated delivery of drugs permit tuning and customization of stimuli to the individual needs and responses of the patient.

According to some embodiments of the invention, the electrodes used for electrical stimulation are arranged as an array on a thin implantable lead. In other embodiments the electrodes are arranged as a two dimensional array of thin implantable leads. In one embodiment the array is disposed in an implantable mesh. A variety of other lead and electrode designs may be used with the invention, including paddle, cuff, and thin wire electrodes, and electrodes on the surface of a leadless SCU.

One embodiment of the invention provides for electrical stimulation and measured response of the individual patient, followed by tuning and controlling of the electrical stimulation by customized programming. Due to variability between individuals in the fine architecture of specific control and response regions of their brains, areas of the brain that may be conducive to acquiring language function may be variously located across a relatively large of the brain. Thus, in embodiment the SCU is connected to a plurality of electrodes disposed in an electrode array that is particularly advantageous for controlled stimulus to a number of different small points across a region of the brain. Delivery of stimulus to multiple sites is expected to reduce accommodation (resistance to stimuli) and encourage adaptation (use of other brain areas to compensate for damaged areas).

The SCU may be programmed to produce either monopolar electrical stimulation, e.g., using the SCU case as an indifferent electrode, or bipolar electrical stimulation, e.g., using one of the electrodes of the electrode array as an indifferent electrode. The SCU may provide for stimulating a nerve or infusing a stimulating substance either intermittently or continuously. Specific stimulation/infusion parameters may provide therapy for, e.g., varying types and degrees of aphasia disorders.

The SCU used with the present invention possesses one or more of the following properties, among other properties:

at least one electrode for applying stimulating current to surrounding tissue and/or a pump and at least one outlet for delivering a drug or drugs to surrounding tissue;

electronic and/or mechanical components encapsulated in a hermetic package made from biocompatible material(s);

electrical circuitry inside the package that receives power and/or receives or transmits data by inductive or radio-frequency (RF) coupling to a transmitting coil placed outside the body, avoiding the need for electrical leads to connect devices to a central implanted or external controller;

a form factor making the SCU implantable in a depression or opening in the skull, or within the brain.

The power source of the SCU is realized using one or more of the following options, or the like:

(1) an external power source coupled to the SCU via an electromagnetic link, for example, via a radio-frequency (RF) link;

(2) a self-contained power source, for example, a primary battery, a replenishable or rechargeable battery, a capacitor, a supercapacitor; and/or (3) if applicable, recharging circuitry for the power source, for example, a RF link, an optical link, or other energy-coupling link.

According to certain embodiments of the invention, an SCU operates independently. According to various embodiments of the invention, an SCU operates in a coordinated manner with other implanted SCUs, other implanted devices, or with devices external to the patient's body.

According to several embodiments of the invention, a SCU incorporates circuitry that senses the disorder or symptoms thereof, or other measures of the state of the patient. Sensed information may be used to control the electrical and/or drug stimulation parameters of the SCU in a closed loop manner. The sensed conditions may include at least one of regional cerebral blood flow (rCBF), impedance, electrical activity of the brain, nerve activity, muscle activity, neurotransmitter level, neurotransmitter breakdown product level and vocal cord vibration. The sensed condition may be detected by positioning a sensor adjacent to one or more of the language areas. According to some embodiments of the invention, the sensing and stimulating circuitry are incorporated into a single SCU. According to other embodiments, the sensing circuitry is remote from the SCU with stimulating circuitry. In some embodiments the sensor transmits signals which are interpreted by an SCU having programmable circuitry.

In one embodiment of the invention a method of treating a patient having aphasia is provided that includes electronically sensing at least one condition indicating a need for stimulus to one or more areas of the brain that has or may have the capacity to develop language functionality. The sensor sends an electronic signal to at least one SCU, thereby activating the SCU, which then activates one or more electrodes and/or drug delivery catheters implanted in or on the brain of the patient to deliver a stimulus to one or more areas of the brain active in communication. In one embodiment the sensed condition is at least one of regional cerebral blood flow (rCBF), impedance, electrical activity of the brain, nerve activity, neurotransmitter level, and neurotransmitter breakdown product level.

In a further embodiment, an implanted system includes a SCU and at least one pump connected to at least one infusion outlet that are together configured to deliver a substance, drug or compound that increases or decreases excitement of at least one area of the brain that exhibits chronic increased or decreased activity in the patient. In one embodiment the substance or compound is one or more of at least one excitatory neurotransmitter (e.g., glutamate, dopamine, norepinephrine, epinephrine, acetylcholine, serotonin), excitatory neurotransmitter agonist (e.g., glutamate receptor agonist, L-aspartic acid, N-methyl-D-aspartic acid (NMDA), bethanechol, norepinephrine), inhibitory neurotransmitter antagonist(s)(e.g., bicuculline), agent that increases the level of an excitatory neurotransmitter (e.g., edrophonium, Mestinon), and/or agent that decreases the level of an inhibitory neurotransmitter (e.g., bicuculline) that may have an excitatory effect on neural tissue.

Conversely, where excessive stimulation results in interference with efforts to communicate, the substance or compound can be at least one of an inhibitory neurotransmitter(s) (e.g., gamma-aminobutyric acid, a.k.a. GABA, dopamine, and glycine), agonist thereof (e.g., a GABA receptor agonist such as midazolam or clonidine, muscimol), excitatory neurotransmitter antagonist(s)(e.g. prazosin, metoprolol, atropine, benztropine), agent that increases the level of an inhibitory neurotransmitter, agent that decreases the level of an excitatory neurotransmitter (e.g., acetylcholinesterase, Group II metabotropic glutamate receptor (mGluR) agonists such as DCG-IV), local anesthetic agent (e.g., lidocaine), and/or an analgesic medication that may have an inhibitory effect on neural tissue. Any of these substances, alone or in combination, may be infused chronically and/or infused acutely in response to a biological signal. Dopamine acts as an excitatory neurotransmitter in some locations and circumstances, and as an inhibitory neurotransmitter in other locations and circumstances.

The above and other aspects of the present invention will be more apparent from the following more particular description thereof, presented in conjunction with the following drawings.

BRIEF DESCRIPTION OF THE DRAWINGS

The above and other aspects of the present invention will be more apparent from the following more particular description thereof, presented in conjunction with the following drawings.

Corresponding reference characters indicate corresponding components throughout the several views of the drawings.

DETAILED DESCRIPTION OF THE INVENTION

Figure 1A:
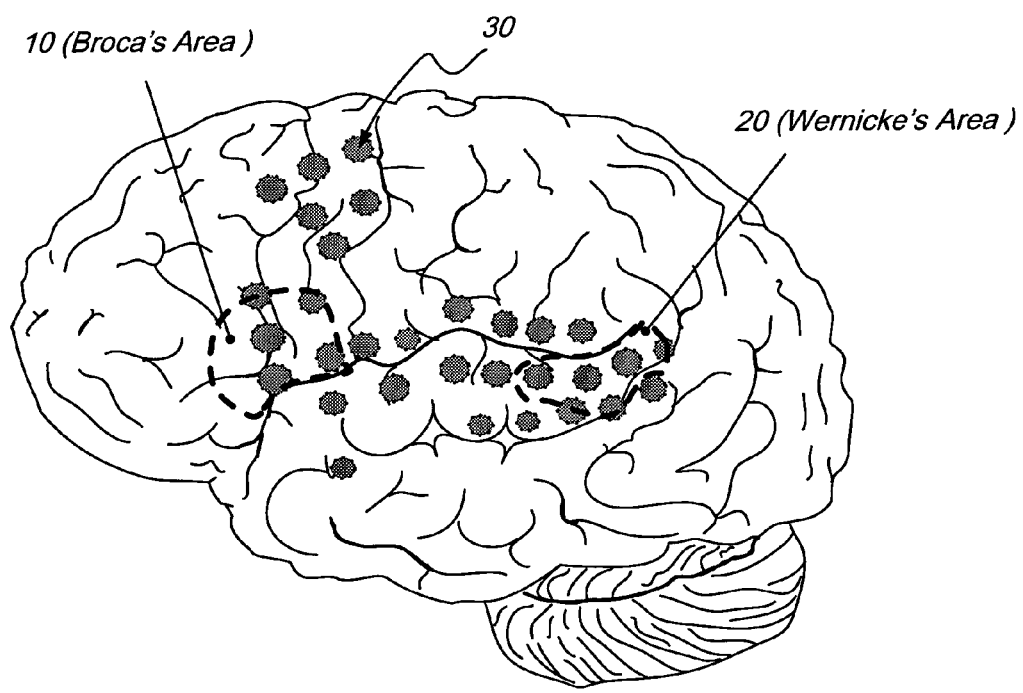
FIG. 1A depicts a lateral surface of the human brain with localization of areas shown to be critical to language in different individuals through electrical mapping.

The following description is of the best mode presently contemplated for carrying out the invention. This description is not to be taken in a limiting sense, but is made merely for the purpose of describing the general principles of the invention. The scope of the invention should be determined with reference to the claims.

ABBREVIATIONS: The following abbreviations are used throughout this application:

| | |
|---|---|
| CPS | a clinician programming system |
| DBS | Deep Brain Stimulation |
| EBCS | external battery charging system |
| fMRI | functional MRI |
| HHP | hand held programmer |
| IPG | implantable signal/pulse generator |
| MDS | manufacturing and diagnostic system |
| MRI | Magnetic Resonance Imaging |
| rCBF | regional cerebral blood flow |
| RF | radio-frequency |
| SCU | system control units |
| TMS | transcranial magnetic stimulation |

The invention disclosed herein provides systems and methods for applying electrical stimulation and/or introducing one or more stimulating drugs to one or more areas of the cortex and/or deep brain for treating or preventing aphasia, as well as the symptoms and pathological consequences thereof.

In adults, localized areas of the brain responsible for language and spatial functions become strongly lateralized to the dominant side of the brain, typically the left, with reduced redundancy as aging progresses. However, there can be functional separation of areas of the brain that perform similar tasks. In bilinguals, there exist distinct language-specific sites as well as shared sites that support both languages. Second language specific sites are reported to be located exclusively in posterior temporal and parietal regions, in contrast to the primary language and shared sites that could be found throughout the mapped regions of the cortex. See e.g. Lucas T H, et al. *J Neurosurg.* 2004 September; 101(3):449-57.

Furthermore, separate areas of the association cortex have some overlapping finctions that allow one part of the brain to compensate functionally for parts that are damaged. This functional compensation has been termed adaptation. For example, fMRI studies have associated activity in the extrasylvian posterior temporal cortex and the right posterior parietal cortex with recovery of comprehension in severe transcortical aphasia. It has been suggested that these areas take over function of damaged areas on the basis of a redundancy recovery mechanism. See e.g. R. Zahn et al. *Brain Res Cogn Brain Res* 18(3)(2004) 322-36.

Two prevalent forms of aphasia, Broca's aphasia and Wernicke's aphasia, were so named by symptoms thought to be due to injuries to either Broca's 10 or Wernicke's areas 20 of the brain as shown on FIG. 1 (depicting the general location of Broca's and Wernicke's areas in dashed encircling lines).

Broca's area of the brain is the motor speech area located in the opercular and triangular regions of the inferior frontal gyrus. The opercular area (area opercularis—Brodmann's area 44) corresponds approximately to the opercular part of the inferior frontal gyrus and is bounded caudally by the inferior precentral sulcus and rostrally by the anterior ascending limb of lateral sulcus. The triangular area (area triangularis—Brodmann's 45) is located in the triangular part of the inferior frontal gyrus and a portion of the orbital part of inferior frontal gyrus. Caudally, the area is bounded by the anterior ascending limb of lateral sulcus, bordering on the insula in the depth of the lateral sulcus. Broca's area is connected electrically via the arcuate fasciculus through the supramarginal gyrus to Wernicke's area. Broca's aphasia typically involves infarcts to the left inferior frontal area, frequently extending to subcortical or insular regions, including the putamen.

Wernicke's area is defined as the perisylvian area of the posterior temporal (also termed superior temporal—Brodmann's area 22) lobe of the left hemisphere of the brain involved in the recognition of spoken words as originally described by Karl Wernicke in the $19^{th}$ century. The infarct responsible for a classic Wernicke's aphasia includes the dominant (typically left-sided) posterior temporal, inferior parietal and lateral temporal-occipital regions.

The inferior parietal cortex of the left hemisphere is active during both procedural and declarative learning and the encoding of unfamiliar faces. Brain lesions to the parietal lobe can result in Gerstmann's syndrome, which is characterized by agraphia/dysgraphia (inability to write), acalculia, finger-agnosia and left-right disorientation. The lateral temporal-occipital cortex forms part of Wernicke's area responsible for receptive/sensory language functions.

Much of what is known about specific locations in the brain that are important for language has come from extra and intraoperative electrical brain mapping studies that were conducted before performing surgery on the brain, including for the treatment of epilepsy. Electrical brain mapping is conducted in the treatment of epilepsy both to identify the site of the lesion as well as to preserve important functions including speech and comprehension, as well as motor, sensory, and visual function. Electrical brain mapping involves the use of direct stimulation of the brain to determine the specific function of a particular area. For example, anomia and speech arrest has been reported to have been induced by stimulation of Broca's area with a 50 Hz wave at 6 mA. See. e.g., M Quigg and N B Fountain. *J. Neurol Neurosurg Psychiatry* 1999; 66: 393-396.

Mapping of areas involving language, sensation, or vision require the patient to actively participate after activation of subdural electrodes typically implanted over the language-dominant left lateral convexity and left basal temporal cortex. Commercially available mapping stimulators are often presently employed including the Ojemann Cortical Stimulator, Radionics, Inc., which provides stimulation with a bipolar electrode having 5 mm spaced tips and delivering a biphasic current with a pulse frequency of 60 Hz and single pulse duration of 1 ms at an amplitude of 2 to 8 mA.

Results of electrical mapping have confirmed that both Broca's and Wernicke's areas play important roles in language comprehension and that the primarily expressive aphasia of patients with lesions of Broca's area results mainly from the predominant participation of Broca's area in language production. See Schaffler L, Luders H O, Beck G J. *Epilepsia.* 1996 May; 37(5):463-75. However, although Broca's and Wernicke's areas of the left hemisphere were classically associated with language, stimulation mapping has shown that cortical sites essential for language have substantial individual variation. See Ojemann G. et al. *J Neurosurgery* 71 (3)(1989) 316-26. The exact location of language function in an individual patient was found to be much smaller that the Broca—Wernicke areas and in some cases lying outside of these traditional areas. Areas identified by Ojemann as critical for language in individual patients are depicted in FIG. 1A in the filled circles 30. Typically individual patients would have one area in the frontal lobe and one or more in the temporal-parietal lobe. Improved fMRI imaging techniques are presently available to help localize key language areas in particular individuals.

Conductive aphasia was classically thought to be caused by disruption of the neural pathways of the arcuate fasciculus, which connect the motor and sensory areas concerned with speech. The arcuate fasciculus (literally "curved bundle") is deep brain neural pathway formed by an arching bundle of association fibers that passes through the frontal, parietal, and temporal lobes and is part of the superior longitudinal fasciculus that interconnects Wernicke's area with Broca's area. The arcuate fasciculus is thus essential for normal speech and language function.

Although lesions most often associated with conduction aphasia are located in white matter underlying the dominant supramarginal gyrus, electrical mapping studies conducted in conjunction with surgical treatment for intractable epilepsy have also identified the posterior, perisylvain cortex, specifically the posterior superior temporal gyrus as associated with conduction aphasia. Quigg M. and Fountain, N B. *J Neurol Neurosurg Psychiatry* 66 (1999) 393-396.

Further injuries to brain structures, including Deep Brain Structures, involved with language include: mutism due to fronto—putaminal lesions; low fluency due to lesions of inferior frontal gyrus and putamen, or anterior centrum semiovale lesions extending to the putamen or the inferior parietal lobulus; repetition disorder, due to external capsule and posterior arm of the internal capsule lesions; oral comprehension disorder, due to injury to the posterior part of temporal gyri extending to the external capsule or the inferior frontal gyus; picture naming impairment and word-finding difficulty depended on a large variety of lesions involving the anterior and posterior cortex, or subcortical regions including the thalamus; verbal paraphasia depended mainly on temporal or caudate lesions; phonemic paraphasia occurring with external capsule damage extending either to the posterior part of the temporal lobe or to the internal capsule; and perseveration due to lesions of the head of caudate nucleus. See e.g. Kreisler, A. et al. *Neurology* 54(5)(2000) 1117-1123; Robles S G, et al., *J Neurol Neurosurg Psychiatry* 76(7) (2005) 940-946.

One embodiment of the present invention exploits the redundancy potential of the brain, as well as the capacity of the brain to develop spatially distinct second language sites, in order to stimulate the growth and/or enhanced development of new or previously underdeveloped language areas that are apart from those damaged. In this embodiment, systems and methods for applying electrical stimulation and/or introducing one or more stimulating drugs to one or more areas of the cortex and/or deep brain are provided for encouraging adaptation and redundancy through the stimulation of areas proximal to the damaged area as well as areas capable of language function but not previously developed in the individual, including the posterior temporal and parietal regions, the extrasylvian posterior temporal cortex, and the right posterior parietal cortex. Other areas of stimulation include the contralateral side of the brain to that damaged. In addition, the present invention provides systems and apparatus for fine electrical control of stimulation parameters and delivery such that adaptation can be enhanced and tuned.

In one embodiment of the invention, treatment locations on the cortex are employed including one or more of the fronto-parietal operculum, lateral temporal-occipital cortex, superior temporal gyrus, posterior parietal cortex, posterior inferior frontal gyrus (Broca's area), and the pre-Rolandic gyrus (inferior precentral). In other embodiments of the invention, treatment locations include deep brain structures including the arcuate fasciculus, putamen, insula, caudate nucleus and the thalamus.

Figure 1B:
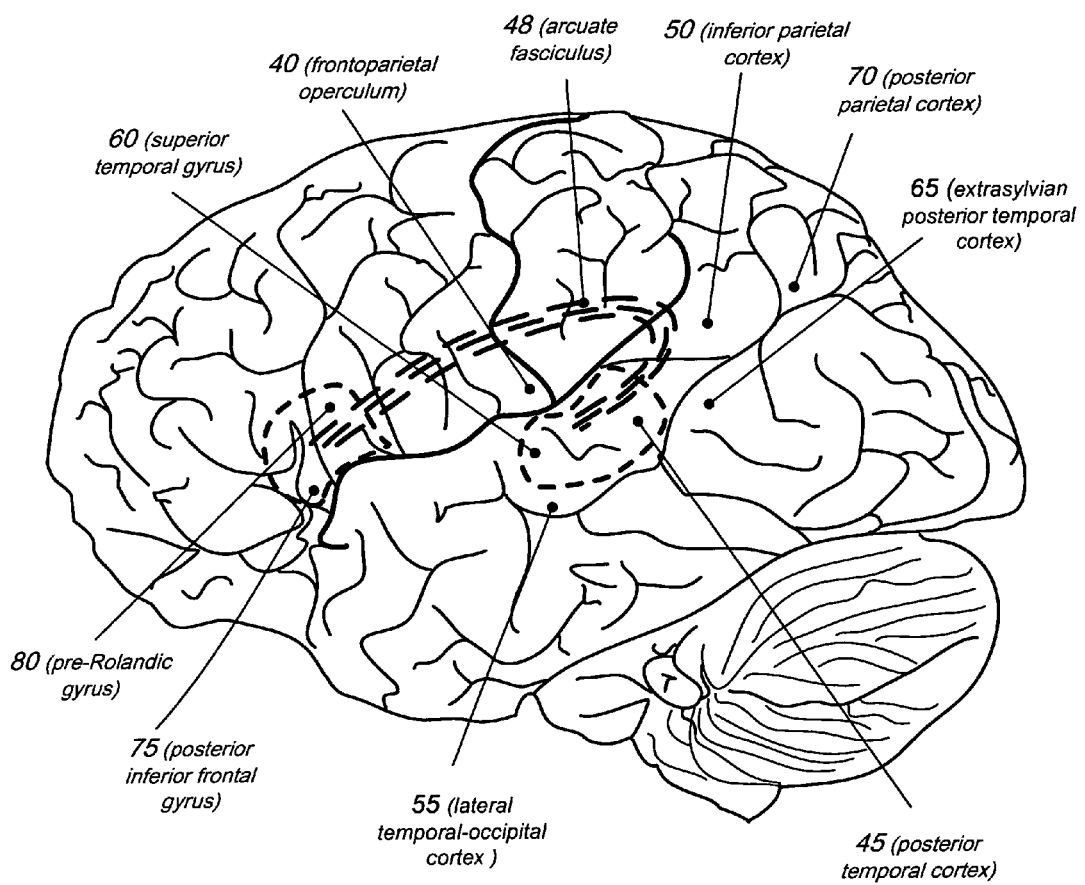
FIG. 1B depicts a lateral surface of the human brain with identification of treatment locations according to some embodiments of the invention.

In one embodiment of the invention, treatment locations on the cortex are employed including one or more of those area generally located on FIG. 1B including the frontoparietal operculum 40, posterior temporal cortex 45, inferior parietal cortex 50, lateral temporal-occipital cortex 55, superior temporal gyrus 60, extrasylvian posterior temporal cortex 65, posterior parietal cortex 70, posterior inferior frontal gyrus (Broca's area) 75, pre-Rolandic gyrus (inferior precentral) 80, and on the arcuate fasciculus 48, which is a deeper connection pathway between the encircled Broca's area and the encircled Wernicke's area. The above mentioned frontoparietal operculum is the part of the cerebrum covering the upper portion of the insula. From anterior to posterior, it consists of the part of the inferior frontal gyrus behind the ascending branch of the lateral sulcus (corresponding to the pars opercularis gyri frontalis inferior), the lower ends of the precentral and postcentral gyri, and the anterior and lower part of the inferior parietal lobule.

Figure 2A:
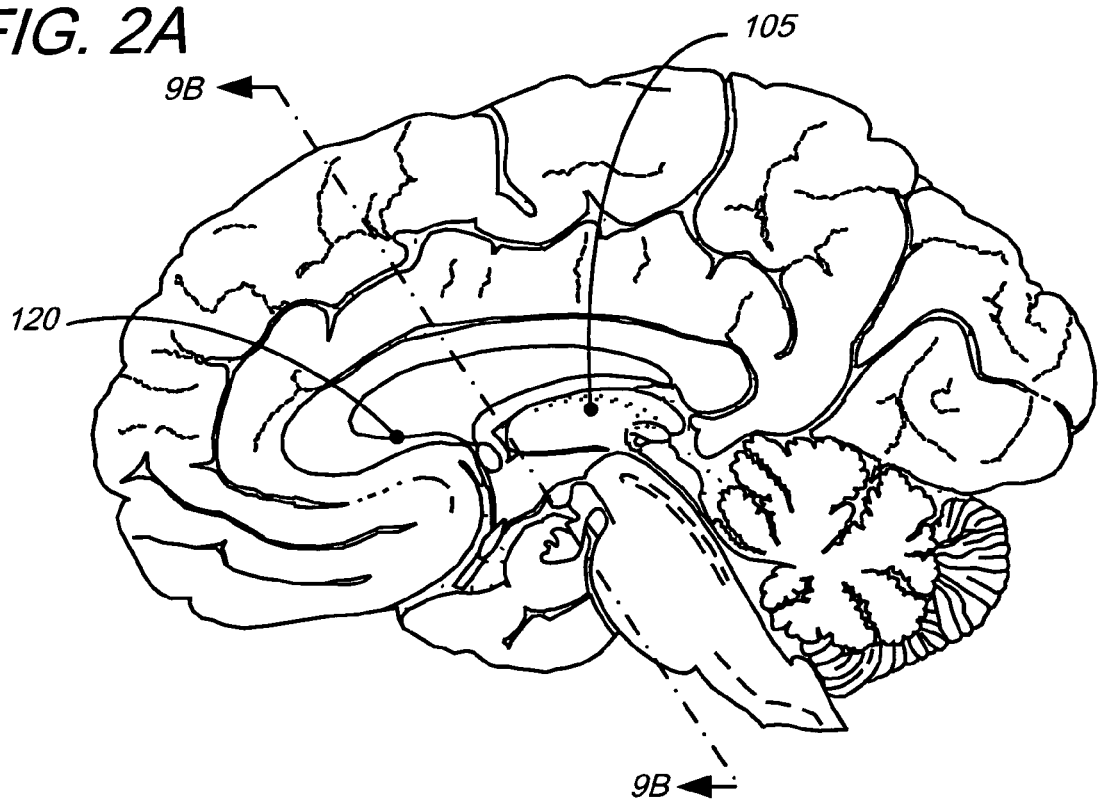
FIG. 2A depicts a sagittal section through the brain with identification of treatment locations according to some embodiments of the invention.
Figure 2B:
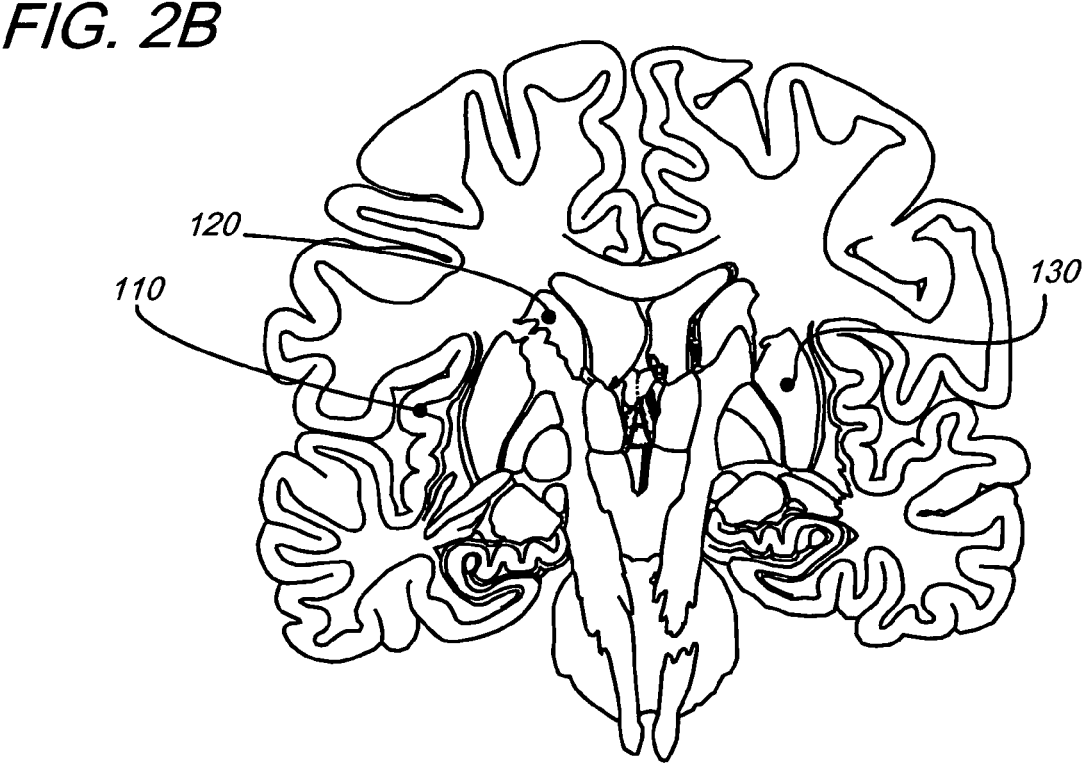
FIG. 2B depicts a coronal section view through the brain depicted in FIG. 2A.

FIG. 2B is a section view through the brain depicted in FIG. 2A, showing the locations of some of the deep brain areas important to language and cognition including the thalamus 105, insula 110, putamen 130 and caudate 120. Thus, in one embodiment of the invention, electrodes and/or drug delivery catheter outflows are positioned in one or more these locations for treatment of aphasia.

The insula 110 (island of Reil) lies deeply in the lateral or Sylvian fissure, beneath the frontal, parietal and temporal opercula, and is surrounded by a deep circular sulcus which separates it from the frontal, parietal, and temporal lobes. The caudate nucleus 120 (nucleus caudatus; caudatum) is a pear-shaped gray mass having its broad area or head directed forward into the anterior cornu of the lateral ventricle and its narrow end, or tail, directed backward on the lateral side of the thalamus. Further areas for electrode and/or drug delivery catheter placement include the putamen 130, especially the dorsal putamen.

In one embodiment of the invention, electrodes are implanted bilaterally in the subthalamic nucleus under stereotactic guidance with imaging and electrophysiologic testing of the location. Thus, in one embodiment of the invention, stimulation of adjacent, distant or contralateral (uninjured) areas of the brain to that damaged is provided to support training of these areas to take over the function of the damaged area (ipsilateral side), ultimately enabling the undamaged areas to accommodate, take over and restore language function.

In the present invention, stimulators and systems are provided that are implantable for long term stimulation as is required for redevelopment of language capabilities. In particular, microstimulators in accordance with the present invention are especially suitable for long term implantation.

In one embodiment of the present invention, the stimulators are flexible in their electrical stimulation capabilities and parameters. Stimulators of one embodiment ofthe present invention are able to deliver electrical stimulation parameters including one or more of: a range of frequency from about 1-650 Hz, a pulse duration of up to about 1550 microseconds, a range of amplitude up to about 15 mA, and combinations thereof. Thus, the implantable stimulators of the present invention are in practice able to be tuned to provide stimulus that supports collateralization and development of new language centers both proximal and distal to the injured areas.

In particular, the present system and method includes use of one ore more System Control Units (SCU) that deliver controlled electrical pulses to specific electrodes. Stimulation parameters are controlled including one or more of: patterns of stimulation, including on/off patterns; pulsewidth; pulse amplitude; repetition rate or pulses per second (pps); electrode configurations including, but not limited to, monopolar, bipolor or tripolar, and combinations thereof. A single electrode or a plurality of electrodes may be implanted including an implanted array of electrodes.

Stimulation can be delivered in response to incoming sounds, e.g. verbs, specific words, the sound of a person talking. The patient can activate the system via a hand held external control unit as they make effort to communicate in response to sounds, images or sensation. Alternatively, SCU can control delivery of stimulation from one or more implanted electrodes, and/drug delivery catheters automatically when the sensed input module conveys a signal. In one embodiment, the system employs SCU having a miniaturized form factor that is advantageous for long term implantation. In one embodiment, the system is powered by an externally rechargeable power source, which, in the context of long term implantation, reduces the need and inherent risks of multiple surgical interventions.

In one embodiment of the invention, individualized stimulation mapping is first conducted followed by implantation of electrodes. Mapping can be conducted intraoperatively by direct cortical stimulation or extraoperatively in two operations, the first of which involves placement of a subdural electrode array. Alternatively, in one embodiment of the invention, a subdural electrode array is implanted for both mapping and then for use in therapeutic stimulation. The array may be left in place for a prolonged or semi-permanent period or as a permanent implant for recovery and treatment of stroke, trauma or surgery induced damage. Stimulus delivered from the array can be tuned via the SCU as treatment progresses. Notably, the stimulation threshold for inducing aphasia varies considerably between patients. For example, using biphasic square wave pulses each of 1 ms at 60 Hz for a train of up to 4 seconds, using 1 mm electrodes 5 mm apart, stimulation thresholds varied from less that 1.5 mA to >10 mA. See Nikas D C, et al. *Techniques in Neurosurgery*, vol 7, no. 1 (2001) 70-84. The present invention provides individualized mapping not only of stimulation sites but also of individual stimulation thresholds and provides a tunable system that is customized to accommodate a range of delivery parameters suitable for the particularities and range of variability between different individuals.

Different electrical stimulation and/or drug infusion parameters may have different effects on neural or other tissue. Therefore, parameters maybe chosen to target specific neural or other tissue populations and/or to exclude others in order to achieve a desired therapeutic effect.

For example, low-frequency electrical stimulation (i.e., less than about 100 Hz for the brain) has been demonstrated to excite neural tissue, leading to increased neural activity. Similarly, excitatory neurotransmitters, agonists thereof, and agents that act to increase levels of an excitatory neurotransmitter(s) have been shown to excite neural tissue, leading to increased neural activity. Inhibitory neurotransmitters have been shown to inhibit neural tissue, leading to decreased neural activity, however, antagonists of inhibitory neurotransmitters and agents that act to decrease levels of an inhibitory neurotransmitter(s) tend to excite neural tissue, leading to increased neural activity.

High-frequency electrical stimulation (i.e., greater than about 100 Hz for the brain) is believed to have an inhibitory effect on neural tissue, leading to decreased neural activity. Similarly, inhibitory neurotransmitters, agonists thereof, and agents that act to increase levels of an inhibitory neurotransmitter(s) have an inhibitory effect on neural tissue, leading to decreased neural activity. Excitatory neurotransmitters have been demonstrated to excite neural tissue, leading to increased neural activity, however, antagonists of excitatory neurotransmitters and agents that act to decrease levels of an excitatory neurotransmitter(s) inhibit neural tissue, leading to decreased neural activity.

The present invention provides electrical and/or drug stimulation to at least one or more of the above mentioned areas as a treatment for aphasia. Herein, the term "drug" refers to medications, anesthetic agents, synthetic or natural hormones, neurotransmitters, cytokines and other intracellular and intercellular chemical signals and messengers, and the like. Certain neurotransmitters, hormones, and other drugs are excitatory for some tissues, yet are inhibitory to other tissues. Therefore, where herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

In some alternatives, an implantable signal generator and electrode(s) and/or an implantable pump and catheter(s) are used to deliver electrical stimulation and/or one or more stimulating drugs to specific areas in the brain. One or more electrodes are surgically implanted in the brain to provide electrical stimulation, and/or one or more catheters are implanted in the brain to infuse the stimulating drug(s).

In some embodiments, electrical stimulation is provided by one or more system control units (SCUs) that are small, implantable stimulators, referred to herein as microstimulators. The microstimulators of the present invention may be similar to or of the type referred to as BION® devices (see FIGS. 3A, 3B, and 3C). The following documents describe various details associated with the manufacture, operation and use of BION implantable microstimulators, and are all incorporated herein by reference:

| Application/Patent/ Publication No. | Filing/Publication Date | Title |
| --- | --- | --- |
| U.S. Pat. No. 5,193,539 | Issued Mar 16, 1993 | Implantable Microstimulator |
| U.S. Pat. No. 5,193,540 | Issued Mar 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued June 28, 1994 | Implantable Microstimulator |
| U.S. Pat. No. 5,405,367 | Issued Apr. 11, 1995 | Structure and Method of Manufacture of an Implantable Microstimulator |
| U.S. Pat. No. 6,208,894 | Issued Mar. 27, 2001 Filed Mar. 25, 1998 | System of implantable devices for monitoring and/or affecting body parameters |
| WO 98/37926 | Pub. Sept. 3, 1998 | Battery-Powered Patient Implantable Device |
| WO 98/43700 | Pub. Oct. 8, 1998 | System of Implantable Devices For Monitoring and/or Affecting Body Parameters |

-continued

| Application/Patent/ Publication No. | Filing/Publication Date | Title |
|---|---|---|
| WO 98/43701 | Pub. Oct. 8, 1998 | System of Implantable Devices For Monitoring and/or Affecting Body Parameters |
| U.S. Pat. No. 6,051,017 (application Ser. No. 09/077,662) | Issued Apr. 18, 2000 (filed May 29, 1998) Pub. Sept., 1997 | Improved Implantable Microstimulator and Systems Employing Same Micromodular Implants to Provide Electrical Stimulation of Paralyzed Muscles and Limbs, by Cameron, et al., published in IEEE Transactions on Biomedical Engineering, Vol. 44, No. 9, pages 781-790. |

Figure 3A:
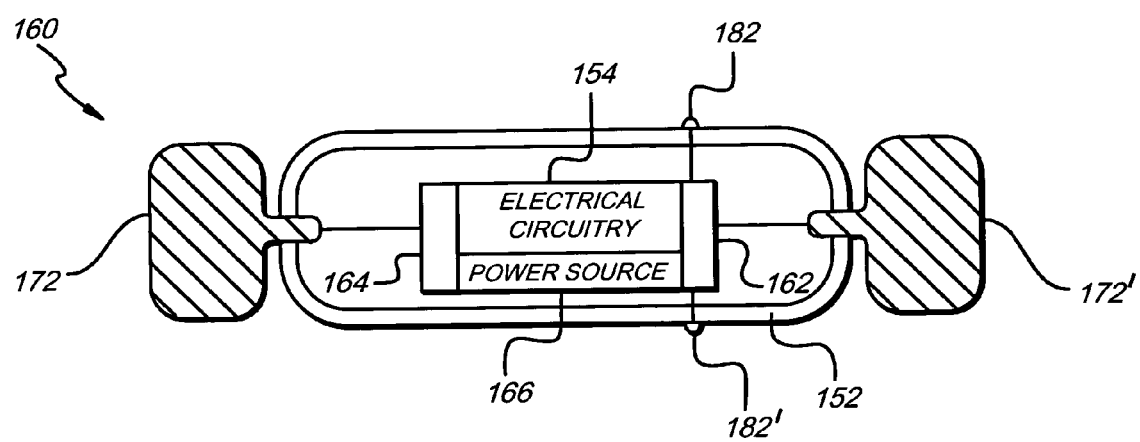
FIGS. 3A, 3B, and 3C show some possible configurations of an implantable microstimulator of the present invention.
Figure 3B:
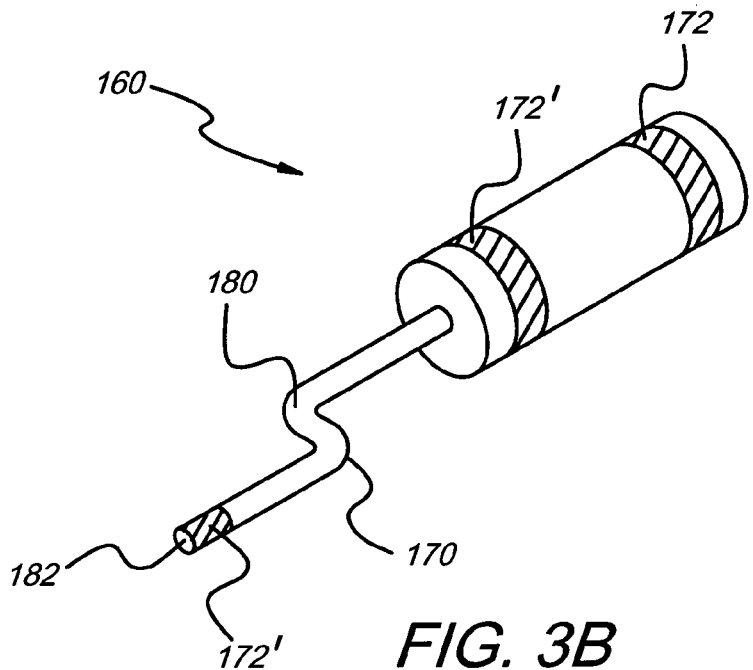
Figure 3C:
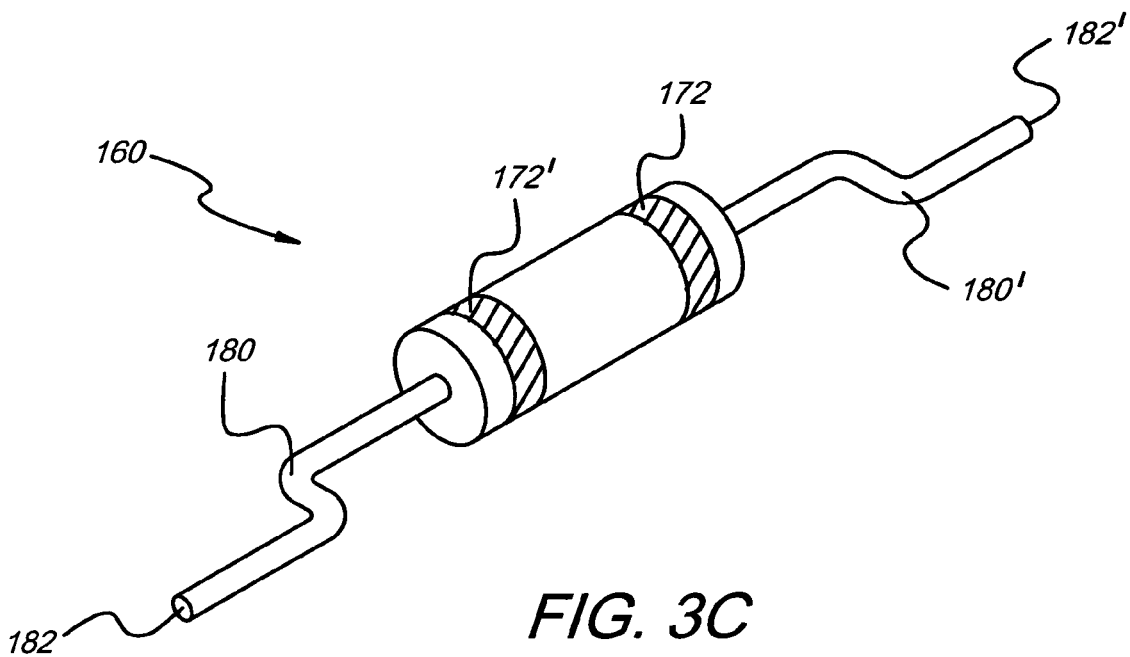

As shown in FIGS. 3A, 3B, and 3C, microstimulator SCUs 160 may include a narrow, elongated capsule 152 containing electronic circuitry 154 connected to electrodes 172 and 172' which may pass through the walls of the capsule at either end. Alternatively, electrodes 172 and/or 172' may be built into the case and/or arranged on a catheter 180 (FIG. 3B) or at the end of a lead, as described below. As detailed in the referenced patents, electrodes 172 and 172' generally comprise a stimulating electrode (to be placed close to the target tissue) and an indifferent electrode (for completing the circuit). Other configurations of microstimulator SCU 160 are possible, as is evident from the above-referenced patent publications, and as described in more detail herein. For example, as depicted in FIG. 3A, SCU 160 may include a rechargeable battery as a power source/storage device 166. SCU 160 also includes, when necessary and/or desired, a programmable memory 164 for storing a set(s) of data, stimulation, and control parameters. Optionally, SCU 160 may include at least one pump 162 in functional communication with inlet/outlets 182 and 182'.

Certain configurations of implantable microstimulator SCU 160 are sufficiently small to permit placement in or adjacent to the structures to be stimulated. For instance, in these configurations, capsule 152 may have a diameter of about 4-5 mm, or only about 3 mm, or even less than about 3 mm. In these configurations, capsule length may be about 25-35 mm, or only about 20-25 mm, or even less than about 20 mm. The shape of the microstimulator may be determined by the structure of the desired target, the surrounding area, and the method of implantation. A thin, elongated cylinder with electrodes at the ends, as shown in FIGS. 3A, 3B, and 3C, is one possible configuration, but other shapes, such as cylinders, disks, spheres, and helical structures, are possible, as are additional electrodes, infusion outlets, leads, and/or catheters.

Microstimulator SCU 160, when certain configurations are used, may be implanted with a surgical insertion tool such as the tool specially designed for the purpose, or may be injected (e.g., via a cannula or hypodermic needle). Alternatively, microstimulator SCU 160 may be implanted via conventional surgical methods, or may be inserted using other endoscopic or laparoscopic techniques. A more complicated surgical procedure may be required for fixing the microstimulator in place. Discussed herein are ways to effectively use such small, fully implantable, chronic neurostimulators for the purpose of treating aphasia.

The external surfaces of microstimulator SCU 160 may advantageously be composed of biocompatible materials. Capsule 152 may be made of, for instance, glass or ceramic to provide a hermetic package that will exclude water vapor but permit passage of electromagnetic fields used to transmit data and/or power. Electrodes 172 and 172' may be made of a noble or refractory metal, such as platinum, iridium, tantalum, titanium, niobium or their alloys, in order to avoid corrosion or electrolysis which could damage the surrounding tissues and the device.

In certain embodiments of the instant invention, microstimulator SCU 160 comprises two, leadless electrodes. However, either or both electrodes 172 and 172' may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of microstimulator SCU 160, while allowing most elements of the microstimulator to be located in a more surgically convenient site. This minimizes the distance traversed and the surgical planes crossed by the device and any lead(s). In most uses of this invention, the leads are no longer than about 150 mm.

As mentioned earlier, stimulation is provided in accordance with the teachings of the present invention by electrical stimulation and/or one or more stimulating drugs. The invention includes one or more system control units (SCUs). In the case of electrical stimulation only, SCUs include a microstimulator and/or an implantable pulse/signal generator (IPG), or the like. In the case of drug infusion only, an SCU comprises an implantable pump or the like. In cases requiring both electrical stimulation and drug infusion, more than one SCU may be used. Alternatively, when needed and/or desired, an SCU provides both electrical stimulation and one or more stimulating drugs.

Figure 4:
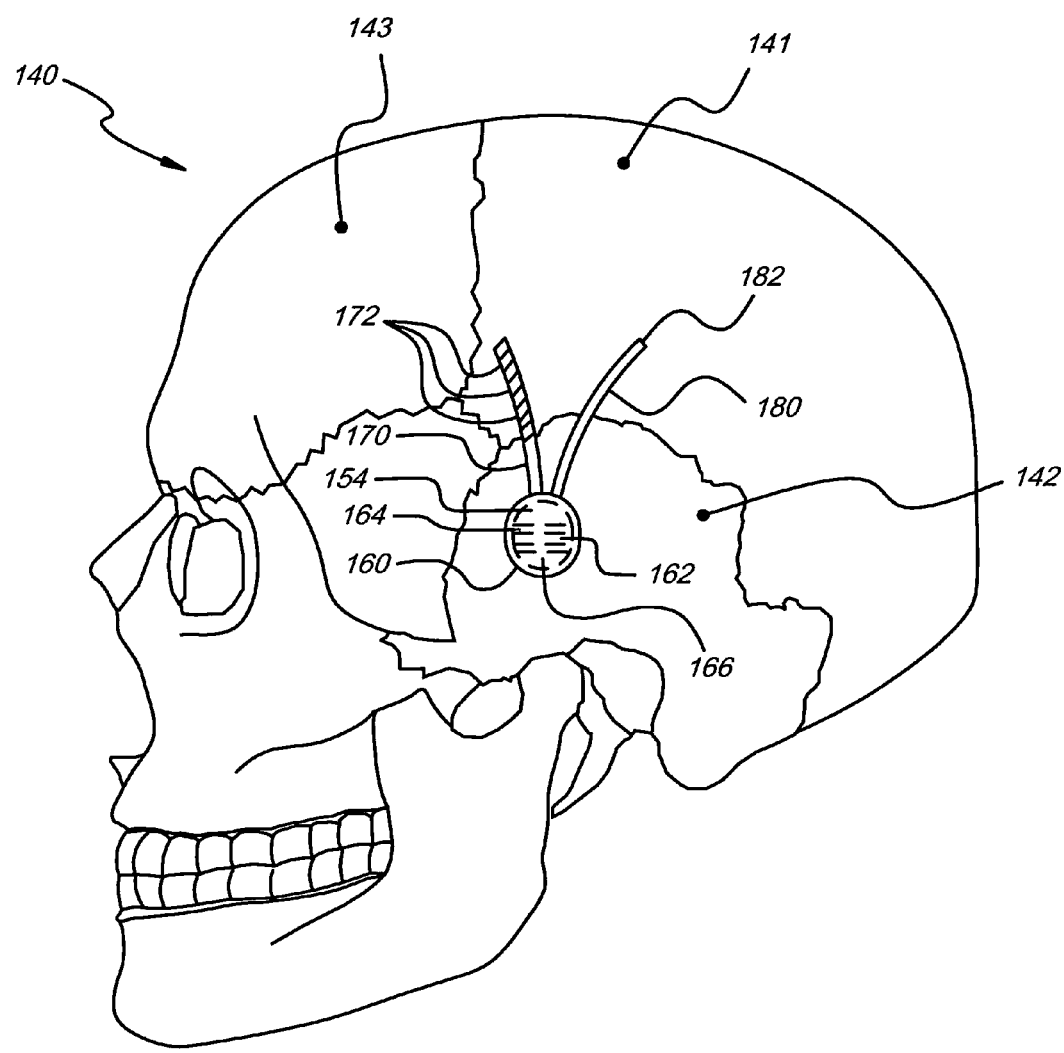
FIG. 4 illustrates a lateral view of the skull and components of some embodiments of the invention.

As depicted in FIG. 4, some embodiments of SCU 160 maybe (but are not necessarily) implanted beneath the scalp, such as in a surgically-created shallow depression or opening in the skull 140, for instance, in parietal bone 141, temporal bone 142, or frontal bone 143. In several embodiments, SCU 160 conforms to the profile of surrounding tissue(s) and/or bone(s), and is small and compact. This may minimize upward pressure applied to the skin or scalp, which pressure may result in skin erosion or infection. In various embodiments, SCU 160 has a diameter of about 75 mm, or only about 65 mm, or even less than about 55 mm. In these configurations, SCU thickness may be approximately 10-12 mm, or even less than about 10 mm.

Figure 5:
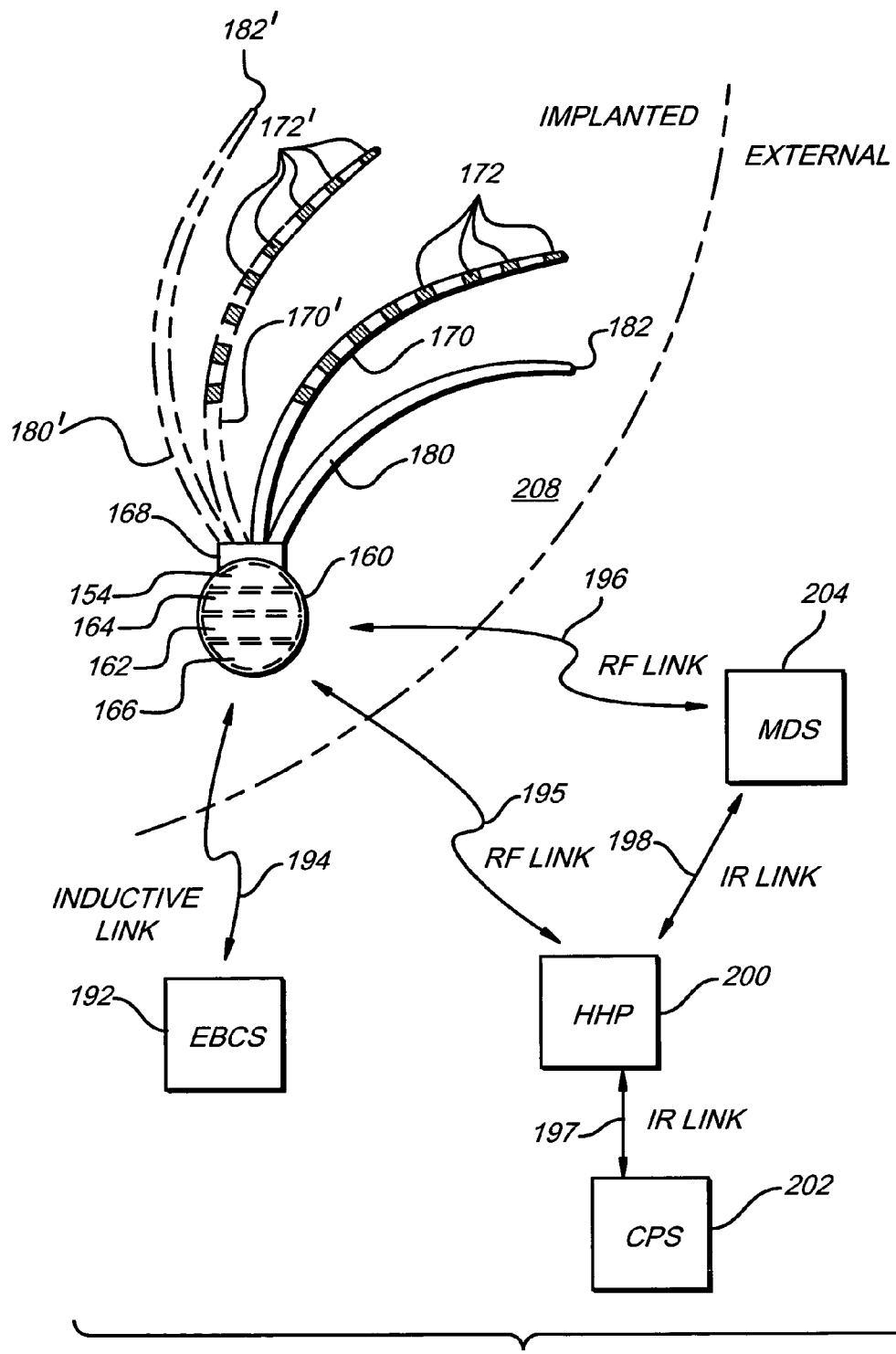
FIG. 5 illustrates internal and external components of certain embodiments of the invention.

As seen in the embodiments depicted in FIG. 5, one or more electrode leads 170 and/or catheters 180 attached to SCU 160 run subcutaneously, for instance, in a surgically-created shallow groove(s) in the skull, to an opening(s) in the skull, and pass through the opening(s) into or onto the brain parenchyma and surrounding tissue. Recessed placement of the SCU and the lead(s) and/or catheter(s) may decrease the likelihood of erosion of overlying skin, and may minimize any cosmetic impact.

In embodiments such as in FIG. 5, electrode(s) 172 are carried on lead 170 having a proximal end coupled to SCU 160. The lead 170 contains wires electrically connecting electrodes 172 to SCU 160. SCU 160 contains electrical components 154 that produce electrical stimulation pulses that travel through the wires of lead 170 and are delivered to electrodes 172, and thus to the tissue surrounding electrodes 172. To protect the electrical components inside SCU 160, some or all of the case of the SCU may be hermetically sealed. For additional protection against, e.g., impact, the case maybe made of metal (e.g. titanium) or ceramic, which materials are also, advantageously, biocompatible. In addition, SCU 160 may be configured to be Magnetic Resonance Imaging (MRI) compatible.

In some alternatives, the electrical stimulation may be provided as described in U.S. Pat. No. 6,920,359 ('359 patent, corresponding to PCT/US01/04417, filed Feb. 12, 2001), which application is incorporated herein by reference in its entirety. As such, the electrical stimulation of the present invention may be as provided in this patent, which is directed to a "Deep Brain Stimulation System for the Treatment of Parkinson's Disease or Other Disorders."

In the case of treatment alternatively or additionally constituting drug infusion, SCU 160 may contain at least one pump 162 for storing and dispensing one or more drugs through infusion outlet(s) 182 and/or catheter(s) 180 into a predetermined site(s) in the brain tissue. When a catheter is used, it includes at least one infusion outlet 182, usually positioned at least at a distal end, while a proximal end of the catheter is connected to SCU 160.

According to some embodiments of the invention, such as described in the previously referenced '359 patent and as depicted in FIG. 5, at least one lead 170 is attached to SCU 160, via a suitable connector 168, if necessary. Each lead includes at least two electrodes 172, and may include as many as sixteen or more electrodes 172. Additional leads 170' and/or catheter(s) 180' may be attached to SCU 160. Hence, FIG. 5 shows (in phantom lines) a second catheter 180', and a second lead 170', having electrodes 172' thereon, also attached to SCU 160. Similarly, the SCUs 160 of FIGS. 3A, 3B, and 3C have outlets 182, 182' for infusing a stimulating drug(s) and electrodes 172, 172' for applying electrical stimulation.

Lead(s) 170 of certain embodiments of the present invention may be less than about 5 mm in diameter, or even less than about 1.5 mm in diameter. Electrodes 172, 172' on leads 170, 170' may be arranged as an array, for instance, as two or more collinear electrodes, or even as four or more collinear electrodes, or they may not be collinear. A tip electrode may also be supplied at the distal end of one or more leads. In some embodiments, SCU 160 is programmable to produce either monopolar electrical stimulation, e.g., using the SCU case as an indifferent electrode, or bipolar electrical stimulation, e.g., using one of the electrodes of the electrode array as an indifferent electrode. Some embodiments of SCU 160 have at least four channels and drive up to sixteen electrodes or more.

SCU 160 (which herein refers to IPGs, implantable pumps, IPG/pump combinations, microstimulators for drug and/or electrical stimulation, other alternative devices described herein, and the like) contains, when necessary and/or desired, electronic circuitry 154 for receiving data and/or power from outside the body by inductive, radio frequency (RF), or other electromagnetic coupling. In some embodiments, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

SCU 160 also includes, when necessary and/or desired, a programmable memory 164 for storing a set(s) of data, stimulation, and control parameters. Among other things, memory 164 may allow electrical and/or drug stimulation to be adjusted to settings that are safe and efficacious with minimal discomfort for each individual. Specific parameters may provide therapy for various aphasia disorders. For instance, some patients may respond favorably to intermittent stimulation, while others may require continuous treatment for relief. In some embodiments, electrical and drug stimulation parameters are controlled independently. In various embodiments, they are coupled, e.g., electrical stimulation is programmed to occur only during drug infusion.

In addition, parameters may be chosen to target specific neural populations and to exclude others, or to increase neural activity in specific neural populations and to decrease neural activity in others. For example, relatively low frequency neurostimulation (i.e., less than about 100 Hz in the brain) typically has an excitatory effect on surrounding neural tissue, leading to increased neural activity, whereas relatively high frequency neurostimulation (i.e., greater than about 100 Hz in the brain) may have an inhibitory effect, leading to decreased neural activity.

Similarly, excitatory neurotransmitters (e.g., acetylcholine), agonists thereof, and agents that increase levels of an excitatory neurotransmitter(s)(e.g., edrophonium) generally have an excitatory effect on neural tissue, while inhibitory neurotransmitters (e.g., gamma-aminobutyric acid, a.k.a. GABA), agonists thereof, and agents that act to increase levels of an inhibitory neurotransmitter(s) generally have an inhibitory effect. However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. atropine) and agents that decrease levels of excitatory neurotransmitters may inhibit neural activity.

Some embodiments of SCU 160 also include a power source and/or power storage device 166. Possible power options for a stimulation device of the present invention, described in more detail below, include but are not limited to an external power source coupled to the stimulation device, e.g., via an RF link, a self-contained power source utilizing any means of generation or storage of energy (e.g., a primary battery, a rechargeable battery such as a lithium ion battery, an electrolytic capacitor, or a super- or ultra-capacitor), and if the self-contained power source is replenishable or rechargeable, means of replenishing or recharging the power source (e.g., an RF link).

In embodiments such as shown in FIG. 5, SCU 160 includes a rechargeable battery as a power source/storage device 166. The battery is recharged, as required, from an external battery charging system (EBCS) 192, typically through an inductive link 194. In these embodiments, and as explained more fully in the earlier referenced '359 patent, SCU 160 includes a processor and other electronic circuitry 154 that allow it to generate stimulation pulses that are applied to a patient 208 through electrodes 172 and/or outlet(s) 182 in accordance with a program and stimulation parameters stored in programmable memory 164. Stimulation pulses of drugs include various types and/or rates of infusion, such as intermittent infusion, infusion at a constant rate, and bolus infusion.

According to certain embodiments of the invention, an SCU operates independently. According to various embodiments of the invention, an SCU operates in a coordinated manner with other SCU(s), other implanted device(s), or other device(s) external to the patient's body. For instance, an SCU may control or operate under the control of another implanted SCU(s), other implanted device(s), or other device(s) external to the patient's body. An SCU may communicate with other implanted SCUs, other implanted devices, and/or devices external to a patient's body via, e.g., an RF link, an ultrasonic link, or an optical link. Specifically, an SCU may communicate with an external remote control (e.g., patient and/or physician programmer) that is capable of sending commands and/or data to an SCU and that may also be capable of receiving commands and/or data from an SCU.

For example, some embodiments of SCU 160 of the present invention may be activated and deactivated, programmed and tested through a hand held programmer (HHP) 200 (which may also be referred to as a patient programmer and may be, but is not necessarily, hand held), a clinician programming system (CPS) 202 (which may also be hand held), and/or a manufacturing and diagnostic system (MDS) 204 (which may also be hand held). HHP 200 may be coupled to SCU 160 via an RF link 195. Similarly, MDS 204 may be coupled to SCU 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to SCU 160 for programming or diagnostic purposes. MDS 204 may also be coupled to SCU 160, either directly through the RF link 196, or indirectly through IR link 198, HHP 200, and RF link 195.

Figure 6:
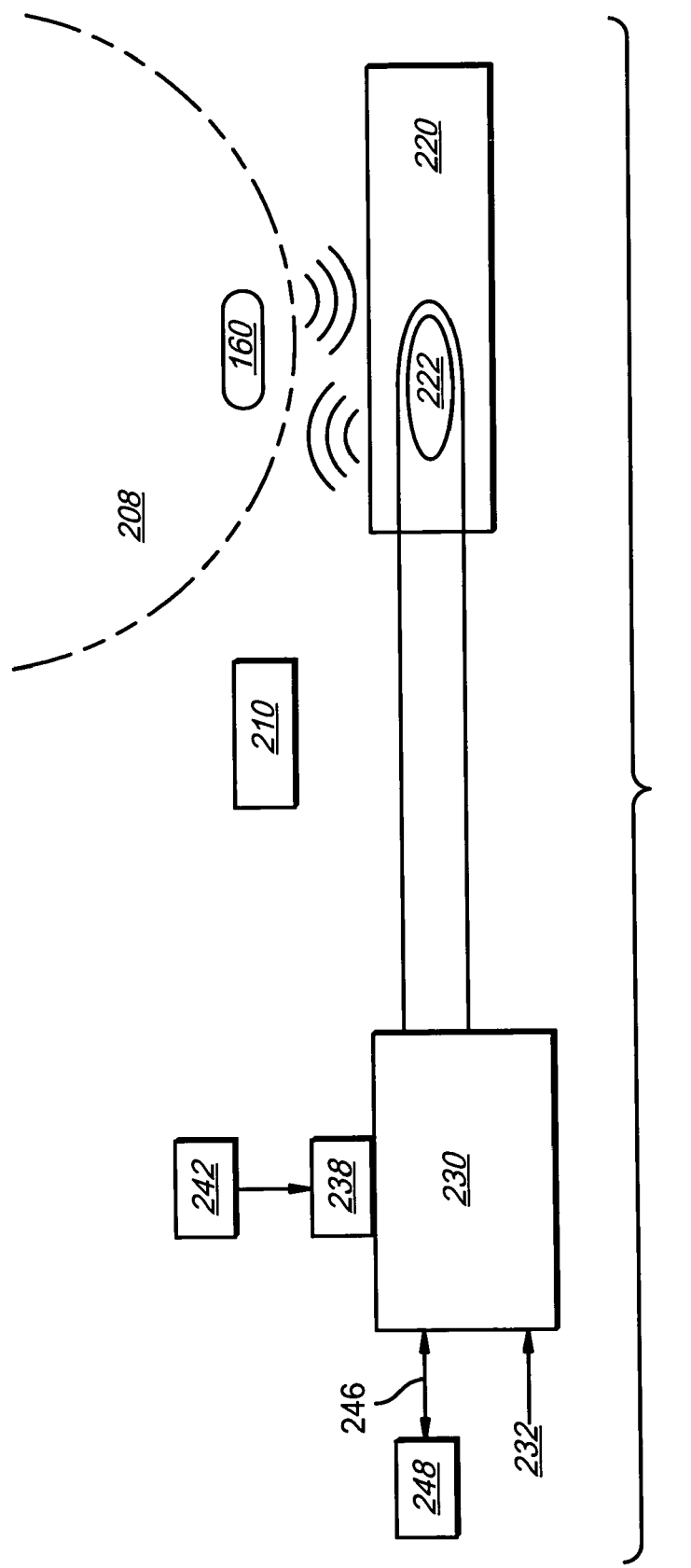
FIG. 6 illustrates external components of various embodiments of the invention.

In certain embodiments, using for example, a BION microstimulator(s) as described in the above referenced patents, and as illustrated in FIG. 6, the patient 208 switches SCU 160 on and off by use of controller 210, which may be handheld. Controller 210 operates to control SCU 160 by any of various means, including sensing the proximity of a permanent magnet located in controller 210, sensing RF transmissions from controller 210, or the like.

External components for programming and providing power to various embodiments of SCU 160 are also illustrated in FIG. 6. When communication with such an SCU 160 is desired, patient 208 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input means 238, e.g., a keypad, whereby the patient 208 or a caregiver 242 may request changes in electrical and/or drug stimulation parameters produced during the normal operation of SCU 160. In these embodiments, manual input means 238 includes various electromechanical switches and/or visual display devices that provide the patient and/or caregiver with information about the status and prior programming of SCU 160.

Alternatively or additionally, external electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

The external appliance(s) may be embedded in a cushion, pillow, or hat. Other possibilities exist, including a head band or other structure that may be affixed to the patient's body or clothing.

In order to help determine the strength and/or duration of electrical stimulation and/or the amount and/or type(s) of stimulating drug(s) required to produce the desired effect, in some embodiments, a patient's response to and/or need for treatment is sensed. For example, electrical activity of the brain (e.g., EEG), nerve activity (e.g., ENG), muscle activity (e.g., EMG), vibration of the vocal cords, or other activity may be sensed. Additionally or alternatively, one or more neurotransmitter levels and/or their associated breakdown product levels may be sensed. For example, levels of one or more neurotransmitters, such as, for example, dopamine, norephinephrine and/or serotonin, may be sensed.

For example, when electrodes of SCU 160 are implanted adjacent to Broca's area, a stimulating electrode of SCU 160, or other sensor, may be used to sense changes in parameters such as electrical activity or blood flow level resulting from the electrical and/or drug stimulation applied to Broca's area. (As used herein, "adjacent" or "near" means as close as reasonably possible to targeted tissue, including touching or even being positioned within the tissue, but in general, may be as far as about 150 mm from the target tissue.)

Alternatively, an "SCU" dedicated to sensory processes, herein a "sensed input module", communicates with an SCU that provides the stimulation pulses. The implant circuitry 154 may, if necessary, amplify and transmit these sensed signals, which may be digital or analog. Other methods of determining the required electrical and/or drug stimulation include measuring electrical activity in various respective regions of the brain as the patient hears, sees or feels a stimulus and attempts to communicate as a consequence. The sensed information may be used to control stimulation parameters in a closed-loop manner.

In other embodiments the present invention, further sensors are provided that function as a "sensed input module." For example, a "sensed input module" that measures speech production can be added which transmits information to a stimulus controller SCU. Initiation of efforts at speech production can be monitored, for example though vibration sensors that detect movement of the vocal cords. The sensed output module SCU uses the sensed information to adjust electrical and/or drug stimulation parameters according to an algorithm programmed, e.g., by a physician. For example, the amplitude of electrical stimulation may be increased in response to increased activity levels. In some alternatives, one SCU performs both the sensing and stimulating functions, as discussed in more detail presently.

While an SCU 160 may also incorporate means of sensing symptoms or other prognostic or diagnostic indicators of efforts to communicate, e.g., via levels of a neurotransmitter or hormone, it may alternatively or desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted SCU(s) 160. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with SCU 160, and may be used to accomplish, potentially among other things, one or more of the following functions:

Function 1: If necessary, transmit electrical power from the external electronic appliance 230 via appliance 220 to SCU 160 in order to power the device and/or recharge the power source/storage device 166. External electronic appliance 230 may include an automatic algorithm that adjusts electrical and/or drug stimulation parameters automatically whenever the SCU(s) 160 is/are recharged.

Function 2: Transmit data from the external appliance 230 via the external appliance 220 to SCU 160 in order to change the parameters of electrical and/or drug stimulation produced by SCU 160.

Function 3: Transmit sensed data indicating a need for treatment or in response to stimulation from SCU 160 (e.g., electrical activity of the brain, nerve activity, muscle activity, neurotransmitter levels, levels of neurotransmitter breakdown products, impedance, vibration, or other activity) to external appliance 230 via external appliance 220.

Function 4: Transmit data indicating state of the SCU 160 (e.g., battery level, drug level, stimulation parameters, etc.) to external appliance 230 via external appliance 220.

By way of example, a treatment modality for aphasia may be carried out according to the following sequence of procedures:

1. An SCU 160 is implanted so that its electrodes 172 and/or infusion outlet 182 are located in or near a language center including one or more of the insula, frontoparietal operculum, posterior temporal cortex, inferior parietal cortex, lateral temporal-occipital cortex, arcuate fasciculus, thalamus, superior temporal gyrus, extrasylvian posterior temporal cortex, posterior parietal cortex, Broca's area (posterior inferior frontal gyrus), pre-Rolandic gyrus (inferior precentral), putamen, insula and/or thalamus.
2. Using Function 2 described above (i.e., transmitting data) of external electronic appliance 230 and external appliance 220, SCU 160 is commanded to produce a series of electrical stimulation pulses, possibly with gradually increasing amplitude, and possibly while infusing gradually increasing amounts of neurotransmitters, or neurotransmitter agonists or antagonists.
3. After each stimulation pulse, or at some other predefined interval, any change in electrical activity originating in the brain, or of neurotransmitters including, for example, glutamate, dopamine, serotonin, acetylcholine, epinephrine, and/or norepinephrine, from the electrical and/or drug stimulation is sensed, for instance, by one or more electrodes 172 and/or 172'. These responses are converted to data and telemetered out to external electronic appliance 230 via Function 3.
4. From the response data received at external appliance 230 from SCU 160, the stimulus threshold for obtaining a response is determined and is used by a clinician 242 acting directly 238 or by other computing means 248 to transmit the desired electrical and/or drug stimulation parameters to SCU 160 in accordance with Function 2.
5. When patient 208 desires to invoke electrical stimulation and/or drug infusion, patient 208 employs controller 210 to set SCU 160 in a state where it delivers a prescribed stimulation pattern from a predetermined range of allowable stimulation patterns.
6. To cease electrical and/or drug stimulation, patient 208 employs controller 210 to turn off SCU 160.
7. Periodically, the patient or caregiver recharges the power source/storage device 166 of SCU 160, if necessary, in accordance with Function 1 described above (i.e., transmit electrical power).

For the treatment of any of the various types and levels of severity of aphasia disorders, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 160, each of which could be separately controlled by means of a digital address. Multiple channels and/or multiple patterns of electrical and/or drug stimulation might thereby be programmed by the clinician and controlled by the patient in order to deal with complex or multiple symptoms or dysfunctions.

In some embodiments discussed earlier, SCU 160, or a group of two or more SCUs, is controlled via closed-loop operation. A need for and/or response to stimulation is sensed via SCU 160, or by an additional SCU (which may or may not be dedicated to the sensing function), or by another implanted or external device. Sensed conditions may be one or more of input sensory information such as sound, visual or touch sensations, vibration, electrical activity of the brain, rCBF or other activity. Additionally or alternatively, neurotransmitter levels and/or their associated breakdown product levels, hormone levels, or other substances, may be sensed. For example, levels of one or more neurotransmitters, e.g., glutamate, dopamine, norepinephrine, epinephrine, acetylcholine, and/or serotonin, may be sensed.

If necessary, the sensed information is transmitted to SCU 160. In some embodiments, the parameters used by SCU 160 are automatically adjusted based on the sensed information. Thus, the electrical and/or drug stimulation parameters are adjusted in a closed-loop manner to provide stimulation tailored to the need for and/or response to the electrical and/or drug stimulation.

Figure 7:
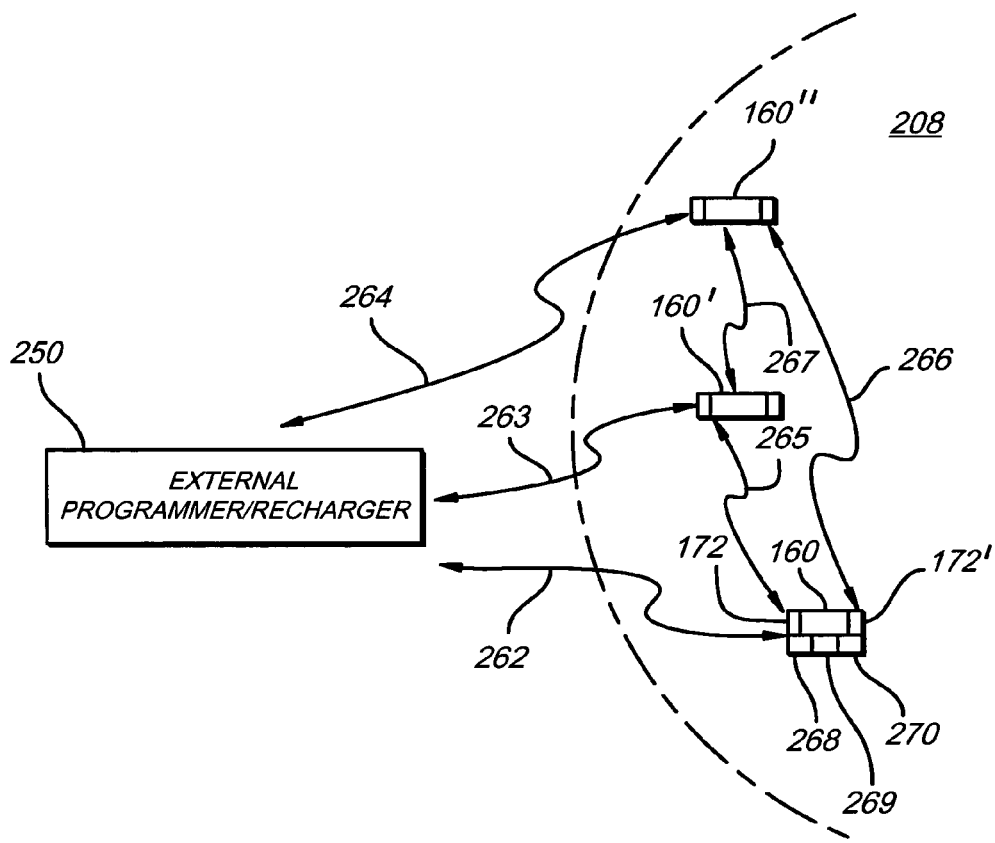
FIG. 7 depicts a system of implantable devices that communicate with each other and/or with external control/programming devices.

For instance, as shown in the example of FIG. 7, a first SCU 160, implanted beneath the skin of the patient 208, provides a first medication or substance; a second SCU 160' provides a second medication or substance; and a third SCU 160" provides electrical stimulation via electrodes 172 and 172'. As mentioned earlier, the implanted devices may operate independently or may operate in a coordinated manner with other similar implanted devices, other implanted devices, or other devices external to the patient's body, as shown by the control lines 262, 263 and 264 in FIG. 7. That is, in accordance with certain embodiments of the invention, the external controller 250 controls the operation of each of the implanted devices 160, 160' and 160". According to various embodiments of the invention, an implanted device, e.g. SCU 160, may control or operate under the control of another implanted device(s), e.g. SCU 160' and/or SCU 160". That is, a device made in accordance with the invention may communicate with other implanted stimulators, other implanted devices, and/or devices external to a patient's body, e.g., via an RF link, an ultrasonic link, an optical link, or the like. Specifically, as illustrated in FIG. 7, SCU 160, 160', and/or 160", made in accordance with the invention, may communicate with an external remote control (e.g., patient and/or physician programmer 250) that is capable of sending commands and/or data to implanted devices and that may also be capable of receiving commands and/or data from implanted devices.

A drug infusion stimulator made in accordance with the invention may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

An SCU made in accordance with the invention thus incorporates, in some embodiments, first sensing means 268 for sensing therapeutic effects such as desired electrical activity in response to communication efforts. The stimulator additionally or alternatively incorporates second means 269 for sensing neurotransmitter levels (e.g., gamma-aminobutyric acid, a.k.a. GABA, dopamine, glycine, glutamate, norepinephrine, epinephrine, acetylcholine, and serotonin) and/or their associated breakdown product levels. The stimulator additionally or alternatively incorporates third means 270 for sensing electrical current levels and/or waveforms supplied by another source of electrical energy. Sensed information may be used to control infusion and/or electrical parameters in a closed loop manner, as shown by control lines 266, 267, and 265. Thus, the sensing means may be incorporated into a device that also includes electrical and/or drug stimulation, or the sensing means (that may or may not have stimulating means) may communicate the sensed information to another device(s) with stimulating means.

Areas which exhibit decreased activity during a given patient's aphasia may experience exacerbation of aphasia with an inhibitory stimulation parameter set and relief of their aphasia with an excitatory stimulation parameter set. Similarly, areas which exhibit increased activity during a given patient's aphasia may experience relief of aphasia with an inhibitory stimulation parameter set and exacerbation of their aphasia with an excitatory stimulation parameter set. Additionally, low amplitude sub-threshold stimulation may enable rehabilitation of aphasia by enhancing the body's natural neuroplasticity mechanisms. Thus, according to some embodiments of the invention, the electrical and/or drug stimulation increases excitement of one or more of those areas of the brain that exhibit chronic decreased activity in patients with aphasia relative to control subjects, thereby treating or preventing symptoms and pathological consequences of aphasia. Such excitatory stimulation is likely to be produced by low-frequency electrical stimulation (e.g., less than about 100 Hz), an excitatory neurotransmitter (e.g., glutamate, dopamine, norepinephrine, epinephrine, acetylcholine, serotonin), an excitatory neurotransmitter agonist (e.g., glutamate receptor agonist, L-aspartic acid, N-methyl-D-aspartic acid (NMDA), bethanechol, norepinephrine), an inhibitory neurotransmitter antagonist(s)(e.g., bicuculline), an agent that increases the level of an excitatory neurotransmitter (e.g., edrophonium, Mestinon), and/or an agent that decreases the level of an inhibitory neurotransmitter (e.g., bicuculline) and thus has an excitatory effect on neural tissue. Other stimulatory neurotransmitters that may be employed include bromocriptine (a dopaminergic agent), amphetamines and piracetam.

According to other embodiments of the invention, the electrical and/or drug stimulation decreases excitement of one or more of those areas of the brain that exhibit chronic increased activity in patients with aphasia relative to control subjects, thereby treating or preventing symptoms and pathological consequences of aphasia. Such inhibitory stimulation is likely to be produced by high-frequency electrical stimulation (e.g., greater than about 100 Hz), an inhibitory neurotransmitter(s)(including e.g., gamma-aminobutyric acid, a.k.a. GABA, dopamine, and glycine), an agonist thereof (e.g., a GABA receptor agonist such as midazolam, an alpha-2 agonist such as clonidine, muscimol), an excitatory neurotransmitter antagonist(s)(e.g. prazosin, metoprolol, atropine, benztropine), an agent that increases the level of an inhibitory neurotransmitter, an agent that decreases the level of an excitatory neurotransmitter (e.g., acetylcholinesterase, Group II metabotropic glutamate receptor (mGluR) agonists such as DCG-IV), a local anesthetic agent (e.g., lidocaine), and/or an analgesic medication that may have an inhibitory effect on neural tissue. Any of these substances, alone or in combination, may be infused chronically and/or infused acutely in response to a biological signal. Dopamine acts as an excitatory neurotransmitter in some locations and circumstances, and as an inhibitory neurotransmitter in other locations and circumstances.

In various embodiments, sensing means described earlier may be used to orchestrate first the activation of SCU(s) targeting an area(s) of the brain, and then, when appropriate, the SCU(s) targeting another area(s) and/or by a different means. Alternatively, this orchestration may be programmed, and not based on a sensed condition.

In one embodiment of the invention implantable microstimulator SCU 160 is sufficiently small to permit placement in or adjacent to the structures to be stimulated. For instance, in these configurations, capsule 152 may have a diameter of about 4-5 mm, or only about 3 mm, or even less than about 3 mm. In these configurations, capsule length may be about 25-35 mm, or only about 20-25 mm, or even less than about 20 mm. Particularly small microstimulators may be particularly desirable in certain patients where injury including stroke injury has affected mobility and coordination and where small microstimulators may be less likely to be cumbersome to the patient.

In one embodiment of the invention, the patient can manually activate the device to provide local stimulation that assists in communicating. Alternatively, an SCU dedicated to sensory processes such as detection of rCBF communicates with an SCU that provides the stimulation pulses and/or drug infusion. In some embodiments, the parameters used by SCU 160 are automatically adjusted based on the sensed information. Thus, the electrical and/or drug stimulation parameters are adjusted in a closed-loop manner to provide stimulation tailored to the need for and/or response to the electrical and/or drug stimulation.

In other embodiments, the SCU is not limited to a miniature form factor. For example, where the electrodes and/or drug infusion catheter outlets are relatively remote from the SCU, the SCU may be a microstimulator or may alternatively be a larger SCU. The remote SCU can be implanted, such as for example percutaneously and connected to the electrodes and/or drug delivery catheters that are also implanted percutaneously. The power source of the SCU is realized using one or more of the following options, or the like: (1) an external power source coupled to the SCU via a radio-frequency (RF) link; (2) a self-contained power source for generation or storage of energy, e.g., a primary battery, a replenishable or rechargeable battery, a capacitor, a supercapacitor; and/or (3) if the self-contained power source is replenishable or rechargeable, replenishing or recharging the power source can be provided by an RF link, an optical link, or other energy-coupling link. The electrodes can be single or multiple and specifically placed. According to some embodiments of the invention, the electrodes used for electrical stimulation are arranged as an array on a thin implantable lead.

Figure 8:
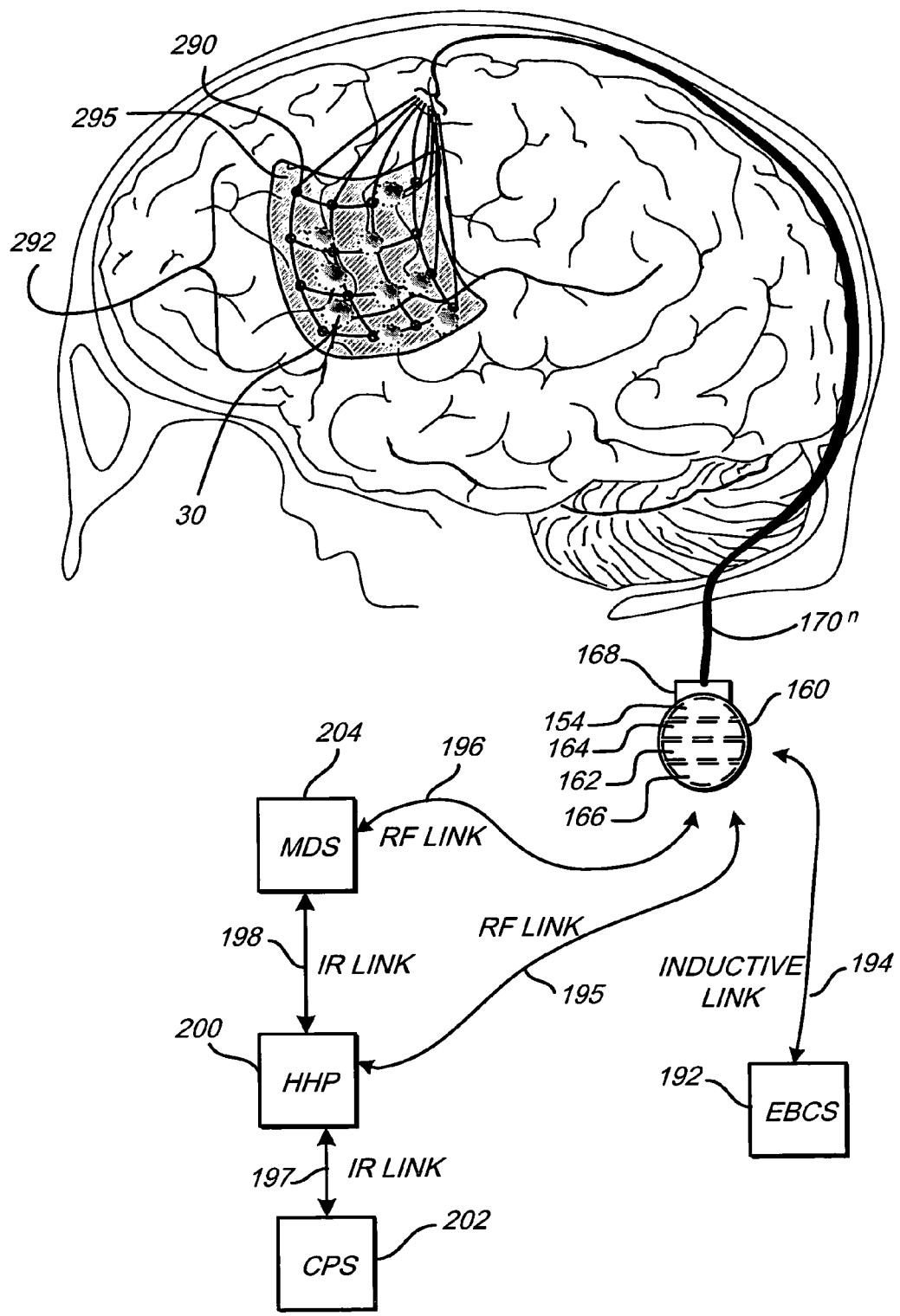
FIG. 8 illustrates an implantable electrode array according to one embodiment of the invention.

In some embodiments, it is desirable develop communication functions in language capable regions that surround an infarcted area and as a consequence relatively large areas of the brain cortex, such as Broca's and/or Wernicke's areas, may be implicated. In such cases, the electrodes can be formed in a two dimensional array or grid that is placed under the skull bones but over the dura of the brain as depicted in FIG. 8. As previously discussed and depicted in FIG. 1, the language center that has been infarcted in the particular patient may be located in any one of a number of possible locations 30. Various of the plurality of individual electrodes 290 in the array 292 can be differentially activated and deactivated according to a variety of stimulation parameters to achieve optimal therapy for the patient and to encourage adaptation. In one embodiment of the invention, the array is embedded in a mesh, such as for example mesh 295. A plurality of leads 170″ may be bundled and connect the array 292 to SCU 160. In one embodiment of the invention, the two dimensional array is first utilized to specifically map areas that are active in the particular patient in response to efforts to communicate and which may be encouraged to take over language function. After the mapping, the two dimensional array may be removed and replaced with individual leads and/or linear electrode arrays or may be left in place as the stimulating electrodes until recovery is deemed sufficient.

Figure 9:
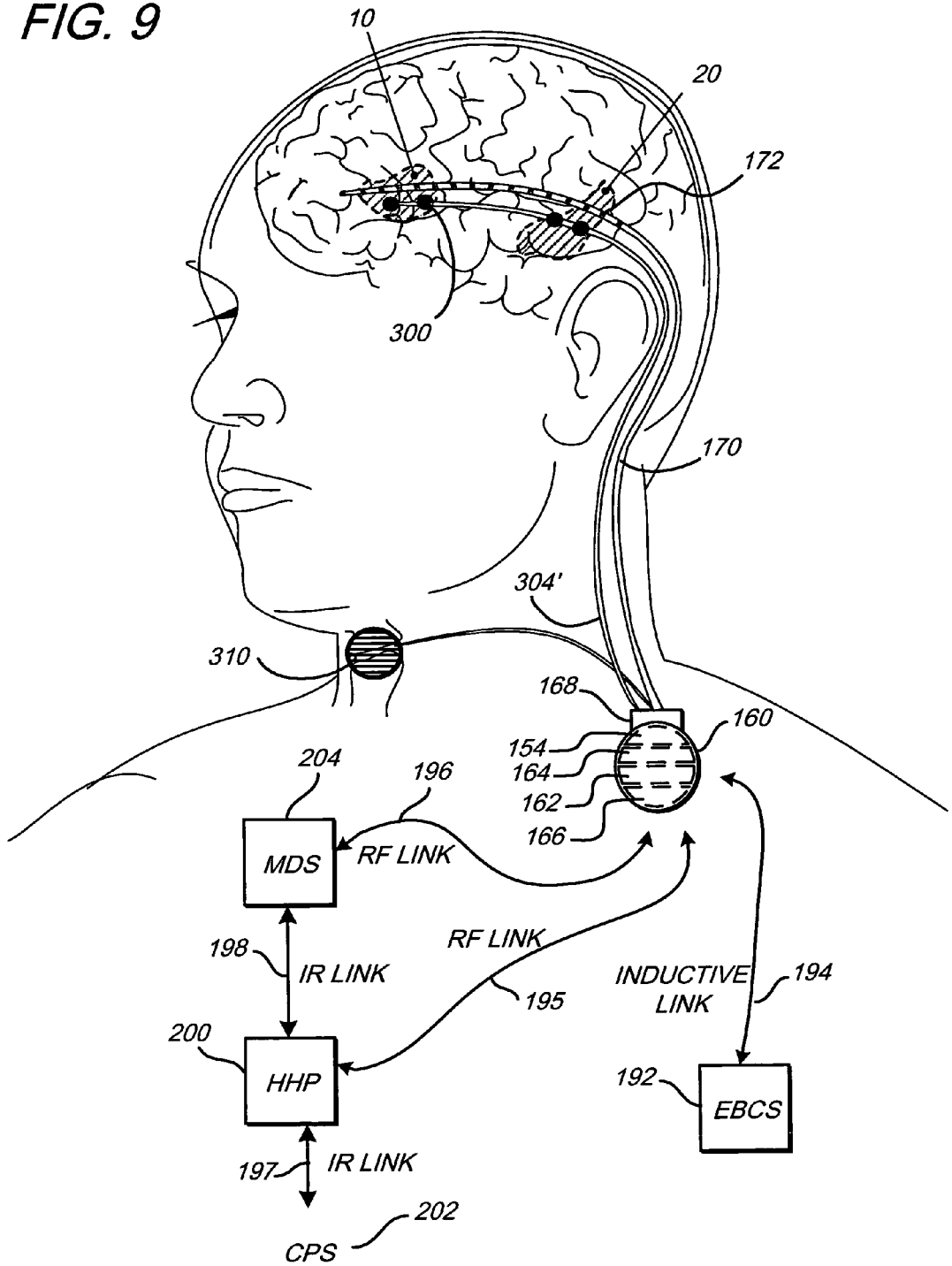
FIG. 9 illustrates an implantable electrode array and optional sensing components according to one embodiment of the invention.

One embodiment of the invention, depicted in FIG. 9, for treatment of Broca's, Wernicke's and or conductive aphasia, involves placement of least one electrode lead 170 on the surface of the cortex in contact with Broca's area 10 and Wernicke's area 20. Each lead includes at least two electrodes 172, and may include as many as sixteen or more electrodes. Lead 170 is attached to SCU 160, via a suitable connector 168, if necessary. Electrodes 172 on leads 170 may be arranged as an array, for instance, as two or more collinear electrodes, or even as four or more collinear electrodes, or they may not be collinear. A tip electrode may also be supplied at the distal end of one or more leads. In some embodiments, SCU 160 is programmable to produce either monopolar electrical stimulation, e.g., using the SCU case as an indifferent electrode, or bipolar electrical stimulation, e.g., using one of the electrodes of the electrode array as an indifferent electrode. Some embodiments of SCU 160 have at least four channels and drive up to sixteen electrodes or more. SCU 160 is programmable to give coordinated electrical pulses to Broca's area 10 and Wernicke's area 20 and thus emulate the normal electrical relationship between these two areas that is mediated by the arcuate fasciculus.

In one optional embodiment of the invention, as depicted in FIG. 9, at least one sensor 300 is in communication with SCU 160 via additional leads 304'. Sensor 300 maybe a sensor for electrical impulses. The sensor additionally or alternatively may sense neurotransmitter levels (e.g., gamma-aminobutyric acid, a.k.a. GABA, dopamine, glycine, glutamate, norepinephrine, epinephrine, acetylcholine, and serotonin) and/or their associated breakdown product levels. For example, in cases of conductive aphasia, Broca's area 10 and Wernicke's area 20 may be normal but a lesion in the arcuate fasciculus prevents communication between these two areas thus causing a failure in appropriate communication. In such cases, receipt of a signal from a sensor 300 located over Broca's area 10 indicates an effort by the patient to communicate. Upon receipt of this signal from sensor 300, SCU 160 is programmed to send stimulating pulses to Wernicke's area 20, thus circumventing the communicative role of the arcuate fasciculus.

In other embodiments of the present invention, a "sensed input module" is optionally added to the system that measures attempted speech production and transmits a corresponding signal to the SCU 160. Initiation of efforts at speech production can be monitored, for example though a vibration sensor 310 that is placed over the vocal fold for detection of movement of the vocal cords. This additional module might be particularly suitable for severe non-communicative aphasia. The SCU uses the sensed information provided by the sensed input module to adjust electrical and/or drug stimulation parameters according to an algorithm programmed, e.g., by a physician. Use of the sensed input module in conjunction with the implanted stimulator essentially provides a feedback loop for "training" desired brain areas for further development. Thus, for example, during a training session the system can be programmed to deliver electrical and/or drug stimulation pulses until vibration over the vocal cords is detected. Electrical stimulus can be modulated and tuned depending on the extent to which the stimulus results in movement of the vocal cords. In this way the patient can essentially "work-out" with the system at their own pace and convenience.

Stimulation at Multiple Sites to Prevent Accommodation: In some individuals and conditions, accommodation, or resistance to stimulation, either subacutely or progressively, may occur if only one center of the brain is stimulated. Thus, in one embodiment of the invention, electrodes are placed in several locations and the stimulation applied to each electrode can be globally or individually addressed depending on response.

While the invention herein disclosed has been described by means of specific embodiments and applications thereof, numerous modifications and variations could be made thereto by those skilled in the art without departing from the scope of the invention set forth in the claims.

What is claimed is:

1. A method of treating a patient with conductive aphasia caused by an abnormally functioning arcuate fasciculus that hinders communication between a Broca's area and a Wernicke's area of the patient's brain, comprising:
   providing at least one System Control Unit (SCU) controllably connected to one or more electrodes and/or infusion outlets;
   implanting the one or more electrodes and/or infusion outlets in or adjacent to the Wernicke's area;
   measuring an attempted speech production of the patient and transmitting a corresponding signal to the SCU; and
   activating the SCU in response to the transmitted signal to control delivery of a stimulus from the one or more electrodes and/or infusion outlets to the Wernicke's area to circumvent the communication role of the arcuate fasciculus, thereby treating or reducing an occurrence or severity of a symptom of the conductive aphasia.

2. The method of claim 1, wherein the SCU is connected to or comprises at least one pump that is operably connected to the one or more infusion ports, and wherein the stimulus comprises stimulation via one or more drugs delivered from the one or more infusion ports through action of the pump.

3. The method of claim 2, wherein the one or more drugs are configured to increase excitement of at least one area of the brain that exhibits chronic decreased activity and wherein the one or more drugs comprise at least one of excitatory neurotransmitters, excitatory neurotransmitter agonists, inhibitory neurotransmitter antagonists, agents that increase the level of an excitatory neurotransmitter, and agents that decrease the level of an inhibitory neurotransmitter.

4. The method of claim 3, wherein the drug that increases excitement of at least one area of the brain that exhibits chronic decreased activity is selected from the group consisting of glutamate, dopamine, norepinephrine, epinephrine, acetylcholine, serotonin, glutamate receptor agonist, L-aspartic acid, N-methyl-D-aspartic acid (NMDA), bethanechol, norepinephrine, bicuculline, edrophonium, and mestinon.

5. The method of claim 2, wherein the one or more drugs are configured to decrease excitement of at least one area of the brain that exhibits chronic increased activity and wherein the one or more drugs comprise at least one of inhibitory neurotransmitters, inhibitory neurotransmitter agonists, excitatory neurotransmitter antagonists, agents that increase the level of an inhibitory neurotransmitter, agents that decrease the level of an excitatory neurotransmitter, anesthetic agents, and analgesic medications.

6. The method of claim 5, wherein drug that decreases excitement of at least one area of the brain that exhibits chronic increased activity is selected from the group consisting of gamma-aminobutyric acid, dopamine, glycine, midazolam, clonidine, muscimol, prazosin, metoprolol, atropine, benztropine, acetyicholinesterase, and Group II metabotropic glutamate receptor agonists.

7. The method of claim 1, wherein one or more of the SCU comprises at least one microstimulator.

8. The method of claim 1, wherein the stimulus is electrical stimulation delivered from the one or more electrodes.

9. The method of claim 1, wherein one or more of the SCU control one or more stimulation parameters selected from the group consisting of: on/off patterns; pulsewidth; pulse amplitude; repetition rate or pulses per second (pps); and electrode configurations.

10. The method of claim 9, wherein the electrode configurations are selected from the group consisting of: monopolar, bipolar, and tripolar.

11. The method of claim 1, wherein the Broca's area and Wernicke's area are both normal.

12. The method of claim 1, wherein the arcuate fasciculus has a lesion that prevents communication between the Broca's area and Wernicke's area.

13. The method of claim 1, wherein the attempted speech production of the patient is measured via one or more sensors implanted within the patient.

14. The method of claim 13, wherein the one or more sensors are implanted adjacent the Broca's area.

* * * * *